United States Patent
Duffy et al.

(10) Patent No.: US 12,343,257 B2
(45) Date of Patent: *Jul. 1, 2025

(54) PROLAPSE PREVENTION DEVICE AND METHODS OF USE THEREOF

(71) Applicant: MEDTRONIC VASCULAR, INC., Santa Rosa, CA (US)

(72) Inventors: Niall Duffy, Galway (IE); David Farascioni, Bethel, CT (US); Adam Fitzgerald, St. Louis Park, MN (US); Nathan Knutson, Long Lake, MN (US); Ana Menk, Shoreview, MN (US); Aran Murray, Galway (IE); Jay Rassat, Buffalo, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/436,319

(22) Filed: Feb. 8, 2024

(65) Prior Publication Data

US 2024/0238091 A1 Jul. 18, 2024

Related U.S. Application Data

(60) Division of application No. 17/674,341, filed on Feb. 17, 2022, now Pat. No. 11,931,261, which is a
(Continued)

(51) Int. Cl.
*A61F 2/24* (2006.01)

(52) U.S. Cl.
CPC .......... *A61F 2/2454* (2013.01); *A61F 2/2466* (2013.01); *A61F 2210/0014* (2013.01);
(Continued)

(58) Field of Classification Search
CPC .... A61F 2/2454; A61F 2/2466; A61F 2/2418; A61F 2210/0014; A61F 2220/0091;
(Continued)

(56) References Cited

U.S. PATENT DOCUMENTS

| 657,597 A | 9/1900 | Hail et al. |
| 6,165,183 A | 12/2000 | Kuehen et al. |

(Continued)

FOREIGN PATENT DOCUMENTS

| IT | UA20162783 A2 | 10/2017 |
| WO | 03/028558 A2 | 4/2003 |
| WO | 2004/030569 A2 | 4/2004 |

OTHER PUBLICATIONS

Notification of Transmittal of The International Search Report and The Written Opinion of The International Searching Authority, or The Declaration issued in International Application No. PCT/US2019/022676, dated Jul. 18, 2019.
(Continued)

*Primary Examiner* — Kathleen S Holwerda

(57) ABSTRACT

A prolapse prevention device formed by a continuous wire-like structure having a first end and a second end disconnected from each other. The continuous wire-like structure is substantially straight in a delivery configuration. The prolapse prevention device in a deployed configuration includes a centering ring of the continuous wire-like structure configured to seat adjacent to and upstream of an annulus of a heart valve in situ, a vertical support of the continuous wire-like structure which extends from the centering ring and includes an apex configured to seat against a roof of an atrium in situ, and a leaflet backstop of the continuous wire-like structure extending radially inward from the centering ring and configured to contact at least at least a first leaflet of the heart valve in situ to exert a pressure in a
(Continued)

downstream direction on the first leaflet to prevent the first leaflet from prolapsing into the atrium.

19 Claims, 19 Drawing Sheets

Related U.S. Application Data continuation of application No. 16/352,976, filed on Mar. 14, 2019, now Pat. No. 11,285,003.

(60) Provisional application No. 62/645,307, filed on Mar. 20, 2018.

(52) U.S. Cl.
CPC .............. *A61F 2220/0008* (2013.01); *A61F 2220/0091* (2013.01); *A61F 2250/001* (2013.01)

(58) Field of Classification Search
CPC ........ A61F 2220/0008; A61F 2250/001; A61F 2/246; A61F 2/2427; A61F 2/2409
See application file for complete search history.

(56) References Cited

U.S. PATENT DOCUMENTS

| | | |
|---|---|---|
| 6,260,552 B1 | 7/2001 | Mortier et al. |
| 6,269,819 B1 | 8/2001 | Oz et al. |
| 6,312,447 B1 | 11/2001 | Grimes |
| 6,332,893 B1 | 12/2001 | Mortier et al. |
| 6,355,030 B1 | 3/2002 | Aldrich et al. |
| 6,402,781 B1 | 6/2002 | Langberg et al. |
| 6,406,420 B1 | 6/2002 | McCarthy et al. |
| 6,419,696 B1 | 7/2002 | Ortiz et al. |
| 6,461,366 B1 | 10/2002 | Seguin |
| 6,537,314 B2 | 3/2003 | Langberg et al. |
| 6,602,288 B1 | 8/2003 | Cosgrove et al. |
| 6,619,291 B2 | 9/2003 | Hlavka et al. |
| 6,626,930 B1 | 9/2003 | Allen et al. |
| 6,629,534 B1 | 10/2003 | St. Goar et al. |
| 6,656,221 B2 | 12/2003 | Taylor et al. |
| 6,676,702 B2 | 1/2004 | Mathis |
| 6,689,164 B1 | 2/2004 | Seguin et al. |
| 6,695,866 B1 | 2/2004 | Kuehen et al. |
| 6,702,826 B2 | 3/2004 | Liddicoat et al. |
| 6,706,065 B2 | 3/2004 | Langberg et al. |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,743,239 B1 | 6/2004 | Keuhn et al. |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,770,083 B2 | 8/2004 | Seguin |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,797,002 B2 | 9/2004 | Spence et al. |
| 6,800,090 B2 | 10/2004 | Alferness et al. |
| 6,805,711 B2 | 10/2004 | Quijano et al. |
| 6,810,882 B2 | 11/2004 | Langberg et al. |
| 6,824,562 B2 | 11/2004 | Mathis et al. |
| 6,840,246 B2 | 1/2005 | Downing |
| 6,875,224 B2 | 4/2005 | Grimes |
| 6,890,353 B2 | 5/2005 | Cohn et al. |
| 6,908,478 B2 | 6/2005 | Alferness et al. |
| 6,913,608 B2 | 7/2005 | Liddicoat et al. |
| 6,926,715 B1 | 8/2005 | Hauck et al. |
| 6,926,730 B1 | 8/2005 | Nguyen et al. |
| 6,949,122 B2 | 9/2005 | Adams et al. |
| 6,960,229 B2 | 11/2005 | Mathis et al. |
| 6,962,605 B2 | 11/2005 | Cosgrove et al. |
| 6,964,683 B2 | 11/2005 | Kowalsky et al. |
| 6,964,684 B2 | 11/2005 | Ortiz et al. |
| 6,966,926 B2 | 11/2005 | Mathis |
| 6,976,995 B2 | 12/2005 | Mathis et al. |
| 6,978,176 B2 | 12/2005 | Lattouf |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,004,958 B2 | 2/2006 | Adams et al. |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,044,967 B1 | 5/2006 | Solem et al. |
| 7,052,487 B2 | 5/2006 | Cohn et al. |
| 7,070,618 B2 | 7/2006 | Streeter |
| 7,077,861 B2 | 7/2006 | Spence |
| 7,077,862 B2 | 7/2006 | Vidlund et al. |
| 7,083,628 B2 | 8/2006 | Bachman |
| 7,090,695 B2 | 8/2006 | Solem et al. |
| 7,094,244 B2 | 8/2006 | Schreck |
| 7,112,207 B2 | 9/2006 | Allen et al. |
| 7,112,219 B2 | 9/2006 | Vidlund et al. |
| 7,122,043 B2 | 10/2006 | Greenhalgh et al. |
| 7,125,420 B2 | 10/2006 | Rourke et al. |
| 7,166,126 B2 | 1/2007 | Spence et al. |
| 7,166,127 B2 | 1/2007 | Spence et al. |
| 7,179,282 B2 | 2/2007 | Alferness et al. |
| 7,179,291 B2 | 2/2007 | Rourke et al. |
| 7,186,264 B2 | 3/2007 | Liddicoat et al. |
| 7,189,199 B2 | 3/2007 | McCarthy et al. |
| 7,192,442 B2 | 3/2007 | Solem et al. |
| 7,192,443 B2 | 3/2007 | Solem et al. |
| 7,211,110 B2 | 5/2007 | Rowe et al. |
| 7,226,467 B2 | 6/2007 | Lucatero et al. |
| 7,229,469 B1 | 6/2007 | Witzel et al. |
| 7,247,134 B2 | 7/2007 | Vidlund et al. |
| 7,270,676 B2 | 9/2007 | Alferness et al. |
| 7,288,097 B2 | 10/2007 | Seguin |
| 7,291,168 B2 | 11/2007 | Macoviak et al. |
| 7,296,577 B2 | 11/2007 | Lashinski et al. |
| 7,300,462 B2 | 11/2007 | Swinford et al. |
| 7,309,354 B2 | 12/2007 | Mathis et al. |
| 7,311,728 B2 | 12/2007 | Solem et al. |
| 7,311,729 B2 | 12/2007 | Mathis et al. |
| 7,311,731 B2 | 12/2007 | Lesniak et al. |
| 7,314,485 B2 | 1/2008 | Mathis |
| 7,316,706 B2 | 1/2008 | Bloom et al. |
| 7,351,259 B2 | 4/2008 | Swinford et al. |
| 7,351,260 B2 | 4/2008 | Nieminen et al. |
| 7,357,815 B2 | 4/2008 | Shaoulian et al. |
| 7,361,190 B2 | 4/2008 | Shaoulian et al. |
| 7,364,588 B2 | 4/2008 | Mathis et al. |
| 7,373,207 B2 | 5/2008 | Lattouf |
| 7,377,941 B2 | 5/2008 | Rhee et al. |
| 7,381,210 B2 | 6/2008 | Zarbatany et al. |
| 7,381,220 B2 | 6/2008 | Macoviak et al. |
| 7,396,364 B2 | 7/2008 | Moaddeb et al. |
| 7,404,824 B1 | 7/2008 | Webler et al. |
| 7,431,692 B2 | 10/2008 | Zollinger et al. |
| 7,431,726 B2 | 10/2008 | Spence et al. |
| 7,442,207 B2 | 10/2008 | Rafiee |
| 7,452,375 B2 | 11/2008 | Mathis et al. |
| 7,464,712 B2 | 12/2008 | Oz et al. |
| 7,473,274 B2 | 1/2009 | Sater |
| 7,485,143 B2 | 2/2009 | Webler et al. |
| 7,500,989 B2 | 3/2009 | Solem et al. |
| 7,503,931 B2 | 3/2009 | Kowalsky et al. |
| 7,503,932 B2 | 3/2009 | Mathis et al. |
| 7,507,252 B2 | 3/2009 | Lashinski et al. |
| 7,509,959 B2 | 3/2009 | Oz et al. |
| 7,510,576 B2 | 3/2009 | Langberg et al. |
| 7,510,577 B2 | 3/2009 | Moaddeb et al. |
| 7,513,908 B2 | 4/2009 | Lattouf |
| 7,527,646 B2 | 5/2009 | Rahdert et al. |
| 7,527,647 B2 | 5/2009 | Spence |
| 7,534,204 B2 | 5/2009 | Starksen et al. |
| 7,534,260 B2 | 5/2009 | Lattouf |
| 7,536,228 B2 | 5/2009 | Shaolian et al. |

(56) References Cited

U.S. PATENT DOCUMENTS

| | | |
|---|---|---|
| 7,559,936 B2 | 7/2009 | Levine et al. |
| 7,563,267 B2 | 7/2009 | Goldfarb et al. |
| 7,563,273 B2 | 7/2009 | Goldfarb et al. |
| 7,569,062 B1 | 8/2009 | Kuehen et al. |
| 7,588,582 B2 | 9/2009 | Ancora |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,120 B2 | 10/2009 | Adams et al. |
| 7,628,797 B2 | 12/2009 | Tieu et al. |
| 7,635,329 B2 | 12/2009 | Goldfarb et al. |
| 7,635,386 B1 | 12/2009 | Gammie |
| 7,635,387 B2 | 12/2009 | Reuter et al. |
| 7,637,945 B2 | 12/2009 | Solem et al. |
| 7,637,946 B2 | 12/2009 | Solem et al. |
| 7,655,015 B2 | 2/2010 | Goldfarb et al. |
| 7,655,040 B2 | 2/2010 | Douk et al. |
| 7,666,193 B2 | 2/2010 | Starksen et al. |
| 7,666,204 B2 | 2/2010 | Thornton et al. |
| 7,666,224 B2 | 2/2010 | Vidlund et al. |
| 7,674,287 B2 | 3/2010 | Alferness et al. |
| 7,682,319 B2 | 3/2010 | Martin et al. |
| 7,682,369 B2 | 3/2010 | Seguin |
| 7,695,510 B2 | 4/2010 | Bloom et al. |
| 7,695,512 B2 | 4/2010 | Lashinski et al. |
| 7,699,892 B2 | 4/2010 | Rafiee et al. |
| 7,704,277 B2 | 4/2010 | Zakay et al. |
| 7,713,298 B2 | 5/2010 | Shaoulian et al. |
| 7,717,954 B2 | 5/2010 | Solem et al. |
| 7,722,523 B2 | 5/2010 | Mortier et al. |
| 7,722,668 B2 | 5/2010 | Moaddeb et al. |
| 7,736,388 B2 | 6/2010 | Goldfarb et al. |
| 7,744,609 B2 | 6/2010 | Allen et al. |
| 7,744,611 B2 | 6/2010 | Nguyen et al. |
| 7,753,858 B2 | 7/2010 | Starksen et al. |
| 7,753,922 B2 | 7/2010 | Starksen |
| 7,753,923 B2 | 7/2010 | St. Goar et al. |
| 7,753,924 B2 | 7/2010 | Starksen et al. |
| 7,758,595 B2 | 7/2010 | Allen et al. |
| 7,758,596 B2 | 7/2010 | Oz et al. |
| 7,758,637 B2 | 7/2010 | Starksen et al. |
| 7,758,639 B2 | 7/2010 | Mathis |
| 7,766,812 B2 | 8/2010 | Schroeder et al. |
| 7,785,366 B2 | 8/2010 | Maurer et al. |
| 7,794,496 B2 | 9/2010 | Gordon et al. |
| 7,803,187 B2 | 9/2010 | Hauser |
| 7,806,928 B2 | 10/2010 | Rowe et al. |
| 7,811,296 B2 | 10/2010 | Goldfarb et al. |
| 7,814,635 B2 | 10/2010 | Gordon et al. |
| 7,828,841 B2 | 11/2010 | Mathis et al. |
| 7,828,842 B2 | 11/2010 | Nieminen et al. |
| 7,828,843 B2 | 11/2010 | Alferness et al. |
| 7,837,728 B2 | 11/2010 | Nieminen et al. |
| 7,837,729 B2 | 11/2010 | Gordon et al. |
| 7,857,846 B2 | 12/2010 | Alferness et al. |
| 7,871,368 B2 | 1/2011 | Zollinger et al. |
| 7,871,433 B2 | 1/2011 | Lattouf |
| 7,883,538 B2 | 2/2011 | To et al. |
| 7,887,552 B2 | 2/2011 | Bachman |
| 7,887,582 B2 | 2/2011 | Mathis et al. |
| 7,914,544 B2 | 3/2011 | Nguyen et al. |
| 7,922,762 B2 | 4/2011 | Starksen |
| 7,927,370 B2 | 4/2011 | Webler et al. |
| 7,931,684 B2 | 4/2011 | Cosgrove et al. |
| 7,935,146 B2 | 5/2011 | Langberg et al. |
| 7,938,827 B2 | 5/2011 | Hauck et al. |
| 7,942,927 B2 | 5/2011 | Kaye et al. |
| 7,942,928 B2 | 5/2011 | Webler et al. |
| 7,955,384 B2 | 6/2011 | Rafiee et al. |
| 7,981,020 B2 | 7/2011 | Mortier et al. |
| 7,981,123 B2 | 7/2011 | Seguin |
| 7,988,725 B2 | 8/2011 | Gross et al. |
| 7,988,726 B2 | 8/2011 | Langberg et al. |
| 7,993,397 B2 | 8/2011 | Lashinski et al. |
| 7,998,151 B2 | 8/2011 | St. Goar et al. |
| 8,016,882 B2 | 9/2011 | Macoviak et al. |
| 8,029,565 B2 | 10/2011 | Lattouf |
| 8,043,368 B2 | 10/2011 | Crabtree |
| 8,052,592 B2 | 11/2011 | Goldfarb et al. |
| 8,057,493 B2 | 11/2011 | Goldfarb et al. |
| 8,062,313 B2 | 11/2011 | Kimblad |
| 8,062,358 B2 | 11/2011 | Mathis et al. |
| 8,066,766 B2 | 11/2011 | To et al. |
| 8,070,746 B2 | 12/2011 | Orton et al. |
| 8,070,805 B2 | 12/2011 | Vidlund et al. |
| 8,075,616 B2 | 12/2011 | Solem et al. |
| 8,092,363 B2 | 1/2012 | Leinsing et al. |
| 8,092,525 B2 | 1/2012 | Eliasen et al. |
| 8,096,985 B2 | 1/2012 | Legaspi et al. |
| 8,100,964 B2 | 1/2012 | Spence |
| 8,109,984 B2 | 2/2012 | Solem et al. |
| 8,123,703 B2 | 2/2012 | Martin et al. |
| 8,128,691 B2 | 3/2012 | Keränen |
| 8,133,239 B2 | 3/2012 | Oz et al. |
| 8,133,272 B2 | 3/2012 | Hyde |
| 8,142,493 B2 | 3/2012 | Spence et al. |
| 8,142,494 B2 | 3/2012 | Rahdert et al. |
| 8,147,542 B2 | 4/2012 | Maisano et al. |
| 8,163,013 B2 | 4/2012 | Machold et al. |
| 8,172,856 B2 | 5/2012 | Eigler et al. |
| 8,172,898 B2 | 5/2012 | Alferness et al. |
| 8,182,529 B2 | 5/2012 | Gordon et al. |
| 8,187,207 B2 | 5/2012 | Machold et al. |
| 8,187,266 B2 | 5/2012 | Dickens et al. |
| 8,187,299 B2 | 5/2012 | Goldfarb et al. |
| 8,187,323 B2 | 5/2012 | Mortier et al. |
| 8,202,315 B2 | 6/2012 | Hlavka et al. |
| 8,211,171 B2 | 7/2012 | Kim et al. |
| 8,216,230 B2 | 7/2012 | Hauck et al. |
| 8,216,256 B2 | 7/2012 | Raschdorf et al. |
| 8,216,302 B2 | 7/2012 | Wilson et al. |
| 8,216,303 B2 | 7/2012 | Navia |
| 8,226,709 B2 | 7/2012 | Groothuis et al. |
| 8,226,711 B2 | 7/2012 | Mortier et al. |
| 8,241,304 B2 | 8/2012 | Bachman |
| 8,241,351 B2 | 8/2012 | Cabiri |
| 8,252,050 B2 | 8/2012 | Maisano et al. |
| 8,262,724 B2 | 9/2012 | Seguin et al. |
| 8,277,502 B2 | 10/2012 | Miller et al. |
| 8,287,555 B2 | 10/2012 | Starksen et al. |
| 8,287,557 B2 | 10/2012 | To et al. |
| 8,303,608 B2 | 11/2012 | Goldfarb et al. |
| 8,303,622 B2 | 11/2012 | Alkhatib |
| 8,323,334 B2 | 12/2012 | Deem et al. |
| 8,328,798 B2 | 12/2012 | Witzel et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,353,956 B2 | 1/2013 | Miller et al. |
| 8,357,195 B2 | 1/2013 | Kuehn |
| 8,361,086 B2 | 1/2013 | Allen et al. |
| 8,382,829 B1 | 2/2013 | Call et al. |
| 8,388,680 B2 | 3/2013 | Starksen et al. |
| 8,409,273 B2 | 4/2013 | Thornton et al. |
| 8,425,504 B2 | 4/2013 | Orton et al. |
| 8,439,971 B2 | 5/2013 | Reuter et al. |
| 8,449,606 B2 | 5/2013 | Eliasen et al. |
| 8,454,656 B2 | 6/2013 | Tuval |
| 8,454,683 B2 | 6/2013 | Rafiee et al. |
| 8,460,370 B2 | 6/2013 | Zakay et al. |
| 8,460,371 B2 | 6/2013 | Hlavka et al. |
| 8,470,028 B2 | 6/2013 | Thornton et al. |
| 8,475,472 B2 | 7/2013 | Bachman |
| 8,486,136 B2 | 7/2013 | Maurer et al. |
| 8,500,761 B2 | 8/2013 | Goldfarb et al. |
| 8,500,800 B2 | 8/2013 | Maisano et al. |
| 8,506,623 B2 | 8/2013 | Wilson et al. |
| 8,506,624 B2 | 8/2013 | Vidlund et al. |
| 8,518,107 B2 | 8/2013 | Tsukashima et al. |
| 8,523,881 B2 | 9/2013 | Cabiri et al. |
| 8,540,620 B2 | 9/2013 | Mortier et al. |
| 8,545,414 B2 | 10/2013 | Fitzgerald et al. |
| 8,545,553 B2 | 10/2013 | Zipory et al. |
| 8,551,161 B2 | 10/2013 | Dolan |

(56) References Cited

U.S. PATENT DOCUMENTS

| | | |
|---|---|---|
| 8,579,967 B2 | 11/2013 | Webler et al. |
| 8,579,968 B1 | 11/2013 | Shannon et al. |
| 8,591,460 B2 | 11/2013 | Wilson et al. |
| 8,608,797 B2 | 12/2013 | Gross et al. |
| 8,632,585 B2 | 1/2014 | Seguin et al. |
| 8,641,727 B2 | 2/2014 | Ancora |
| 8,647,254 B2 | 2/2014 | Callas et al. |
| 8,663,322 B2 | 3/2014 | Keränen |
| 8,690,858 B2 | 4/2014 | Machold et al. |
| 8,690,939 B2 | 4/2014 | Miller et al. |
| 8,709,074 B2 | 4/2014 | Solem et al. |
| 8,715,342 B2 | 5/2014 | Zipory et al. |
| 8,721,665 B2 | 5/2014 | Oz et al. |
| 8,728,097 B1 | 5/2014 | Sugimoto et al. |
| 8,734,467 B2 | 5/2014 | Miller et al. |
| 8,734,505 B2 | 5/2014 | St. Goar et al. |
| 8,740,918 B2 | 6/2014 | Seguin |
| 8,740,920 B2 | 6/2014 | Goldfarb et al. |
| 8,753,373 B2 | 6/2014 | Chau et al. |
| 8,758,257 B2 | 6/2014 | Cecere et al. |
| 8,758,393 B2 | 6/2014 | Zentgraf |
| 8,758,432 B2 | 6/2014 | Solem et al. |
| 8,771,292 B2 | 7/2014 | Allen et al. |
| 8,777,966 B2 | 7/2014 | Dale et al. |
| 8,778,016 B2 | 7/2014 | Janovsky et al. |
| 8,778,017 B2 | 7/2014 | Eliasen et al. |
| 8,784,482 B2 | 7/2014 | Rahdert et al. |
| 8,784,483 B2 | 7/2014 | Navia |
| 8,790,394 B2 | 7/2014 | Miller et al. |
| 8,795,298 B2 | 8/2014 | Hernlund et al. |
| 8,795,352 B2 | 8/2014 | O'Beirne et al. |
| 8,808,368 B2 | 8/2014 | Maisano et al. |
| 8,821,570 B2 | 9/2014 | Dumontelle et al. |
| 8,845,717 B2 | 9/2014 | Khairkhahan et al. |
| 8,845,723 B2 | 9/2014 | Spence et al. |
| 8,852,213 B2 | 10/2014 | Gammie et al. |
| 8,858,622 B2 | 10/2014 | Machold et al. |
| 8,858,623 B2 | 10/2014 | Miller et al. |
| 8,864,822 B2 | 10/2014 | Spence et al. |
| 8,888,843 B2 | 11/2014 | Khairkhanan et al. |
| 8,888,844 B2 | 11/2014 | Eliasen et al. |
| 8,894,705 B2 | 11/2014 | Eliasen et al. |
| 8,911,461 B2 | 12/2014 | Traynor et al. |
| 8,911,494 B2 | 12/2014 | Hammer et al. |
| 8,920,322 B2 | 12/2014 | Mansi et al. |
| 8,926,695 B2 | 1/2015 | Gross et al. |
| 8,926,696 B2 | 1/2015 | Cabiri et al. |
| 8,926,697 B2 | 1/2015 | Gross et al. |
| 8,932,348 B2 | 1/2015 | Solem et al. |
| 8,938,283 B2 | 1/2015 | Zentgraf et al. |
| 8,940,042 B2 | 1/2015 | Miller et al. |
| 8,940,044 B2 | 1/2015 | Hammer et al. |
| 8,945,177 B2 | 2/2015 | Dell et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,956,406 B2 | 2/2015 | Subramanian et al. |
| 8,956,407 B2 | 2/2015 | Macoviak et al. |
| 8,961,597 B2 | 2/2015 | Subramanian et al. |
| 8,968,335 B2 | 3/2015 | Robinson et al. |
| 8,968,393 B2 | 3/2015 | Rothstein |
| 8,974,445 B2 | 3/2015 | Warnking et al. |
| 8,974,525 B2 | 3/2015 | Nieminen et al. |
| 8,979,923 B2 | 3/2015 | Spence et al. |
| 8,979,925 B2 | 3/2015 | Chang et al. |
| 8,992,605 B2 | 3/2015 | Zakai et al. |
| 8,998,794 B2 | 4/2015 | Mortier et al. |
| 8,998,933 B2 | 4/2015 | Rothstein et al. |
| 9,011,463 B2 | 4/2015 | Adams et al. |
| 9,011,468 B2 | 4/2015 | Ketai et al. |
| 9,011,520 B2 | 4/2015 | Miller et al. |
| 9,011,530 B2 | 4/2015 | Reich et al. |
| 9,011,531 B2 | 4/2015 | Rourke et al. |
| 9,044,221 B2 | 6/2015 | Zentgraf et al. |
| 9,044,246 B2 | 6/2015 | Goldfarb et al. |
| 9,050,187 B2 | 6/2015 | Sugimoto et al. |
| 9,060,858 B2 | 6/2015 | Thornton et al. |
| 9,066,710 B2 | 6/2015 | Dale et al. |
| 9,107,658 B2 | 8/2015 | Schaller et al. |
| 9,107,750 B2 | 8/2015 | Cartledge et al. |
| 9,119,718 B2 | 9/2015 | Keränen |
| 9,119,719 B2 | 9/2015 | Zipory et al. |
| 9,125,632 B2 | 9/2015 | Loulmet et al. |
| 9,125,653 B2 | 9/2015 | Kovach |
| 9,131,928 B2 | 9/2015 | Zlotnick et al. |
| 9,131,939 B1 | 9/2015 | Call et al. |
| 9,168,137 B2 | 10/2015 | Subramanian et al. |
| 9,173,646 B2 | 11/2015 | Fabro |
| 9,179,896 B2 | 11/2015 | Machold et al. |
| 9,180,005 B1 | 11/2015 | Lashinski et al. |
| 9,180,006 B2 | 11/2015 | Keranen |
| 9,180,007 B2 | 11/2015 | Reich et al. |
| 9,180,008 B2 | 11/2015 | Yellin et al. |
| 9,192,374 B2 | 11/2015 | Zentgraf |
| 9,192,471 B2 | 11/2015 | Bolling |
| 9,192,472 B2 | 11/2015 | Gross et al. |
| 9,198,757 B2 | 12/2015 | Schroeder et al. |
| 9,216,018 B2 | 12/2015 | Sutherland et al. |
| 9,226,787 B2 | 1/2016 | Merryman et al. |
| 9,226,825 B2 | 1/2016 | Starksen et al. |
| 9,232,942 B2 | 1/2016 | Seguin et al. |
| 9,232,998 B2 | 1/2016 | Wilson et al. |
| 9,237,886 B2 | 1/2016 | Seguin et al. |
| 9,254,141 B2 | 2/2016 | Morris et al. |
| 9,259,218 B2 | 2/2016 | Robinson |
| 9,259,261 B2 | 2/2016 | Boronyak et al. |
| 9,259,317 B2 | 2/2016 | Wilson et al. |
| 9,265,608 B2 | 2/2016 | Miller et al. |
| 9,271,833 B2 | 3/2016 | Kim et al. |
| 9,277,994 B2 | 3/2016 | Miller et al. |
| 9,282,964 B1 | 3/2016 | Cohen et al. |
| 9,301,842 B2 | 4/2016 | Bielefeld |
| 9,314,242 B2 | 4/2016 | Bachman |
| 9,320,600 B2 | 4/2016 | Nieminen et al. |
| 9,326,857 B2 | 5/2016 | Cartledge et al. |
| 9,345,470 B2 | 5/2016 | Tuval |
| 9,351,830 B2 | 5/2016 | Gross et al. |
| 9,358,111 B2 | 6/2016 | Spence et al. |
| 9,358,112 B2 | 6/2016 | Hlavka et al. |
| 9,370,424 B2 | 6/2016 | Call et al. |
| 9,393,080 B2 | 7/2016 | Zentgraf et al. |
| 9,402,721 B2 | 8/2016 | Buchbinder et al. |
| 9,408,695 B2 | 8/2016 | Mathis et al. |
| 9,414,852 B2 | 8/2016 | Gifford et al. |
| 9,414,918 B2 | 8/2016 | Chau et al. |
| 9,414,921 B2 | 8/2016 | Miller et al. |
| 9,421,098 B2 | 8/2016 | Gifford et al. |
| 9,421,099 B2 | 8/2016 | Dolan |
| 9,427,237 B2 | 8/2016 | Oz et al. |
| 9,433,503 B2 | 9/2016 | Tsukashima et al. |
| 9,445,898 B2 | 9/2016 | Tuval et al. |
| 9,452,048 B2 | 9/2016 | O'Beirne et al. |
| 9,474,605 B2 | 10/2016 | Rowe et al. |
| 9,474,606 B2 | 10/2016 | Zipory et al. |
| 9,474,608 B2 | 10/2016 | Mathis et al. |
| 9,492,276 B2 | 11/2016 | Lee et al. |
| 9,498,228 B2 | 11/2016 | Dale et al. |
| 9,498,330 B2 | 11/2016 | Solem |
| 9,498,331 B2 | 11/2016 | Chang et al. |
| 9,504,570 B2 | 11/2016 | Hauser et al. |
| 9,510,829 B2 | 12/2016 | Goldfarb et al. |
| 9,510,837 B2 | 12/2016 | Seguin |
| 9,510,946 B2 | 12/2016 | Chau et al. |
| 9,510,948 B2 | 12/2016 | Padala et al. |
| 9,526,613 B2 | 12/2016 | Gross et al. |
| 9,526,614 B2 | 12/2016 | Keränen |
| 9,526,616 B2 | 12/2016 | Nieminen et al. |
| 9,532,874 B2 | 1/2017 | Griffin et al. |
| 9,545,305 B2 | 1/2017 | Wilson et al. |
| 9,561,104 B2 | 2/2017 | Miller et al. |
| 9,561,105 B2 | 2/2017 | Rowe |
| 9,572,666 B2 | 2/2017 | Basude et al. |
| 9,572,667 B2 | 2/2017 | Solem |
| 9,579,200 B2 | 2/2017 | Lederman et al. |

(56) References Cited

U.S. PATENT DOCUMENTS

| | | |
|---|---|---|
| 9,592,118 B2 | 3/2017 | Khairkhahan et al. |
| 9,592,122 B2 | 3/2017 | Zipory et al. |
| 9,597,184 B2 | 3/2017 | Machold et al. |
| 9,610,082 B2 | 4/2017 | Morris et al. |
| 9,610,161 B2 | 4/2017 | Macoviak et al. |
| 9,610,162 B2 | 4/2017 | Zipory et al. |
| 9,610,163 B2 | 4/2017 | Khairkhahan et al. |
| 9,615,926 B2 | 4/2017 | Lashinski et al. |
| 9,616,197 B2 | 4/2017 | Serina et al. |
| 9,622,862 B2 | 4/2017 | Lashinski et al. |
| 9,636,106 B2 | 5/2017 | Meier et al. |
| 9,636,107 B2 | 5/2017 | Morales et al. |
| 9,636,223 B2 | 5/2017 | Khalil et al. |
| 9,636,224 B2 | 5/2017 | Zipory et al. |
| 9,642,706 B2 | 5/2017 | Eidenschink |
| 9,649,106 B2 | 5/2017 | Nobles et al. |
| 9,662,205 B2 | 5/2017 | Eidenschink |
| 9,662,208 B2 | 5/2017 | Padala et al. |
| 9,662,209 B2 | 5/2017 | Gross et al. |
| 9,706,996 B2 | 7/2017 | Nguyen et al. |
| 11,285,003 B2 * | 3/2022 | Duffy .................. A61F 2/2454 |
| 2001/0005787 A1 | 6/2001 | Oz et al. |
| 2002/0183837 A1 | 12/2002 | Streeter et al. |
| 2003/0105519 A1 | 6/2003 | Fasol et al. |
| 2003/0120340 A1 | 6/2003 | Liska et al. |
| 2003/0120341 A1 | 6/2003 | Shennib et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0044350 A1 | 3/2004 | Martin et al. |
| 2004/0102839 A1 | 5/2004 | Cohn et al. |
| 2004/0127982 A1 | 7/2004 | Machold et al. |
| 2004/0127983 A1 | 7/2004 | Mortier et al. |
| 2004/0133063 A1 | 7/2004 | McCarthy et al. |
| 2004/0133240 A1 | 7/2004 | Adams et al. |
| 2004/0138745 A1 * | 7/2004 | Macoviak ............ A61F 2/2454 623/2.14 |
| 2004/0152947 A1 | 8/2004 | Schroeder et al. |
| 2004/0153144 A1 | 8/2004 | Seguin et al. |
| 2004/0158321 A1 | 8/2004 | Reuter et al. |
| 2004/0162610 A1 | 8/2004 | Liska et al. |
| 2004/0167539 A1 | 8/2004 | Kuehen et al. |
| 2004/0210240 A1 | 10/2004 | Saint |
| 2004/0220654 A1 | 11/2004 | Mathis et al. |
| 2004/0220657 A1 | 11/2004 | Nieminen et al. |
| 2004/0243227 A1 | 12/2004 | Starksen et al. |
| 2004/0254600 A1 | 12/2004 | Zarbatany et al. |
| 2004/0260394 A1 | 12/2004 | Douk et al. |
| 2004/0267083 A1 | 12/2004 | McCarthy et al. |
| 2005/0027351 A1 | 2/2005 | Rueter et al. |
| 2005/0033446 A1 | 2/2005 | Deem et al. |
| 2005/0049679 A1 | 3/2005 | Taylor et al. |
| 2005/0070999 A1 | 3/2005 | Spence |
| 2005/0071000 A1 | 3/2005 | Liddicoat et al. |
| 2005/0075723 A1 | 4/2005 | Schroeder et al. |
| 2005/0107810 A1 | 5/2005 | Morales et al. |
| 2005/0107811 A1 | 5/2005 | Starksen et al. |
| 2005/0107871 A1 | 5/2005 | Realyvasquez et al. |
| 2005/0137449 A1 | 6/2005 | Nieminen et al. |
| 2005/0137450 A1 | 6/2005 | Aronson et al. |
| 2005/0143811 A1 | 6/2005 | Realyvasquez |
| 2005/0148815 A1 | 7/2005 | Mortier et al. |
| 2005/0149014 A1 | 7/2005 | Hauck et al. |
| 2005/0159810 A1 | 7/2005 | Filsoufi |
| 2005/0177228 A1 | 8/2005 | Solem et al. |
| 2005/0184122 A1 | 8/2005 | Hlavka et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0209690 A1 | 9/2005 | Mathis et al. |
| 2005/0216039 A1 | 9/2005 | Lederman |
| 2005/0216078 A1 | 9/2005 | Starksen et al. |
| 2005/0222488 A1 | 10/2005 | Chang et al. |
| 2005/0222489 A1 | 10/2005 | Rahdert et al. |
| 2005/0228422 A1 | 10/2005 | Machold et al. |
| 2005/0240202 A1 | 10/2005 | Shennib et al. |
| 2005/0267529 A1 | 12/2005 | Crockett et al. |
| 2005/0267574 A1 | 12/2005 | Cohn et al. |
| 2005/0273138 A1 | 12/2005 | To et al. |
| 2005/0288777 A1 | 12/2005 | Rhee et al. |
| 2005/0288778 A1 | 12/2005 | Shaoulian et al. |
| 2006/0015178 A1 | 1/2006 | Moaddeb et al. |
| 2006/0025787 A1 | 2/2006 | Morales et al. |
| 2006/0069429 A1 | 3/2006 | Spence et al. |
| 2006/0100699 A1 | 5/2006 | Vidlund et al. |
| 2006/0106278 A1 | 5/2006 | Machold et al. |
| 2006/0106279 A1 | 5/2006 | Machold et al. |
| 2006/0122633 A1 | 6/2006 | To et al. |
| 2006/0136053 A1 | 6/2006 | Rourke et al. |
| 2006/0149368 A1 | 7/2006 | Spence |
| 2006/0161040 A1 | 7/2006 | McCarthy et al. |
| 2006/0161169 A1 | 7/2006 | Nieminen et al. |
| 2006/0167474 A1 | 7/2006 | Bloom et al. |
| 2006/0178700 A1 | 8/2006 | Quinn |
| 2006/0184230 A1 | 8/2006 | Solem et al. |
| 2006/0184242 A1 | 8/2006 | Lichtenstein |
| 2006/0195012 A1 | 8/2006 | Mortier et al. |
| 2006/0206203 A1 | 9/2006 | Yang et al. |
| 2006/0229708 A1 | 10/2006 | Powell et al. |
| 2006/0241745 A1 | 10/2006 | Solem |
| 2006/0241746 A1 | 10/2006 | Shaoulian et al. |
| 2006/0252984 A1 | 11/2006 | Rahdert et al. |
| 2006/0271174 A1 | 11/2006 | Nieminen et al. |
| 2006/0281968 A1 | 12/2006 | Duran et al. |
| 2006/0282161 A1 | 12/2006 | Huynh et al. |
| 2006/0293698 A1 | 12/2006 | Douk |
| 2007/0027533 A1 | 2/2007 | Douk |
| 2007/0038293 A1 | 2/2007 | St. Goar et al. |
| 2007/0038297 A1 | 2/2007 | Bobo et al. |
| 2007/0050022 A1 | 3/2007 | Vidlund et al. |
| 2007/0055206 A1 | 3/2007 | To et al. |
| 2007/0055368 A1 | 3/2007 | Rhee et al. |
| 2007/0061010 A1 | 3/2007 | Hauser et al. |
| 2007/0066863 A1 | 3/2007 | Rafiee et al. |
| 2007/0067027 A1 | 3/2007 | Moaddeb et al. |
| 2007/0073391 A1 | 3/2007 | Bourang et al. |
| 2007/0078297 A1 | 4/2007 | Rafiee et al. |
| 2007/0080188 A1 | 4/2007 | Spence et al. |
| 2007/0100356 A1 | 5/2007 | Lucatero et al. |
| 2007/0100439 A1 | 5/2007 | Cangialosi et al. |
| 2007/0112244 A1 | 5/2007 | McCarthy et al. |
| 2007/0112424 A1 | 5/2007 | Spence et al. |
| 2007/0118151 A1 | 5/2007 | Davidson |
| 2007/0118215 A1 | 5/2007 | Moaddeb |
| 2007/0129737 A1 | 6/2007 | Goldfarb et al. |
| 2007/0135913 A1 | 6/2007 | Moaddeb et al. |
| 2007/0156235 A1 | 7/2007 | Rourke et al. |
| 2007/0173926 A1 | 7/2007 | Bobo et al. |
| 2007/0185571 A1 | 8/2007 | Kapadia et al. |
| 2007/0198038 A1 | 8/2007 | Cohen et al. |
| 2007/0203391 A1 | 8/2007 | Bloom et al. |
| 2007/0213758 A1 | 9/2007 | Rourke et al. |
| 2007/0232941 A1 | 10/2007 | Rabinovich |
| 2007/0233238 A1 | 10/2007 | Huynh et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0255396 A1 | 11/2007 | Douk et al. |
| 2007/0265658 A1 | 11/2007 | Nelson et al. |
| 2007/0265702 A1 | 11/2007 | Lattouf |
| 2007/0270803 A1 | 11/2007 | Lattouf |
| 2007/0276437 A1 | 11/2007 | Call et al. |
| 2007/0276478 A1 | 11/2007 | Marmureanu et al. |
| 2007/0282429 A1 | 12/2007 | Hauser et al. |
| 2007/0293943 A1 | 12/2007 | Quinn |
| 2008/0004597 A1 | 1/2008 | Lattouf et al. |
| 2008/0015688 A1 | 1/2008 | Hill et al. |
| 2008/0039935 A1 | 2/2008 | Buch et al. |
| 2008/0050347 A1 | 2/2008 | Ichim |
| 2008/0065205 A1 | 3/2008 | Nguyen et al. |
| 2008/0091059 A1 | 4/2008 | Machold et al. |
| 2008/0091264 A1 | 4/2008 | Machold et al. |
| 2008/0140188 A1 | 6/2008 | Rahdert et al. |

(56) References Cited

U.S. PATENT DOCUMENTS

| | | |
|---|---|---|
| 2008/0140190 A1 | 6/2008 | Macoviak et al. |
| 2008/0167714 A1 | 7/2008 | St. Goar et al. |
| 2008/0177380 A1 | 7/2008 | Starksen et al. |
| 2008/0183283 A1 | 7/2008 | Downing |
| 2008/0183285 A1 | 7/2008 | Shaoulian et al. |
| 2008/0195126 A1 | 8/2008 | Solem |
| 2008/0195200 A1 | 8/2008 | Vidlund et al. |
| 2008/0200981 A1 | 8/2008 | Shaoulian et al. |
| 2008/0228032 A1 | 9/2008 | Starksen et al. |
| 2008/0228201 A1 | 9/2008 | Zarbatany et al. |
| 2008/0228265 A1 | 9/2008 | Spence et al. |
| 2008/0228266 A1 | 9/2008 | McNamara et al. |
| 2008/0228272 A1 | 9/2008 | Moaddeb et al. |
| 2008/0234701 A1 | 9/2008 | Morales et al. |
| 2008/0234702 A1 | 9/2008 | Morales et al. |
| 2008/0234813 A1 | 9/2008 | Heuser |
| 2008/0243150 A1 | 10/2008 | Starksen et al. |
| 2008/0249504 A1 | 10/2008 | Lattouf et al. |
| 2008/0249618 A1 | 10/2008 | Huynh et al. |
| 2008/0319541 A1 | 12/2008 | Filsoufi |
| 2009/0043381 A1 | 2/2009 | Macoviak et al. |
| 2009/0069885 A1 | 3/2009 | Rahdert et al. |
| 2009/0076600 A1 | 3/2009 | Quinn |
| 2009/0088838 A1 | 4/2009 | Shaolian et al. |
| 2009/0118744 A1 | 5/2009 | Wells et al. |
| 2009/0118825 A1 | 5/2009 | Rourke et al. |
| 2009/0132036 A1 | 5/2009 | Navia |
| 2009/0149949 A1 | 6/2009 | Quinn |
| 2009/0177266 A1 | 7/2009 | Powell et al. |
| 2009/0182418 A1 | 7/2009 | Solem et al. |
| 2009/0182419 A1 | 7/2009 | Bolling |
| 2009/0209950 A1 | 8/2009 | Starksen |
| 2009/0216322 A1 | 8/2009 | Le et al. |
| 2009/0222081 A1 | 9/2009 | Linder et al. |
| 2009/0228100 A1 | 9/2009 | Solem et al. |
| 2009/0287179 A1 | 11/2009 | Machold et al. |
| 2009/0299471 A1* | 12/2009 | Keranen ............... A61F 2/2442 623/2.37 |
| 2009/0306622 A1 | 12/2009 | Machold et al. |
| 2009/0306685 A1 | 12/2009 | Fill |
| 2009/0326648 A1 | 12/2009 | Machold et al. |
| 2010/0023056 A1 | 1/2010 | Johansson et al. |
| 2010/0023118 A1 | 1/2010 | Medlock et al. |
| 2010/0030330 A1 | 2/2010 | Bobo et al. |
| 2010/0036483 A1 | 2/2010 | Rourke et al. |
| 2010/0049213 A1 | 2/2010 | Serina et al. |
| 2010/0094248 A1 | 4/2010 | Nguyen et al. |
| 2010/0121349 A1 | 5/2010 | Meier et al. |
| 2010/0121433 A1 | 5/2010 | Bolling et al. |
| 2010/0121435 A1 | 5/2010 | Subramanian et al. |
| 2010/0121437 A1 | 5/2010 | Subramanian et al. |
| 2010/0131057 A1 | 5/2010 | Subramanian et al. |
| 2010/0137887 A1 | 6/2010 | Crockett et al. |
| 2010/0152845 A1 | 6/2010 | Bloom et al. |
| 2010/0161044 A1 | 6/2010 | Chang et al. |
| 2010/0185172 A1 | 7/2010 | Fabro |
| 2010/0185273 A1 | 7/2010 | Solem et al. |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2010/0210899 A1 | 8/2010 | Schankereli |
| 2010/0217283 A1 | 8/2010 | St. Goar et al. |
| 2010/0249920 A1 | 9/2010 | Bolling et al. |
| 2010/0280602 A1 | 11/2010 | Mathis |
| 2010/0298929 A1 | 11/2010 | Thornton et al. |
| 2010/0298930 A1 | 11/2010 | Orlov |
| 2010/0318184 A1 | 12/2010 | Spence |
| 2010/0331971 A1 | 12/2010 | Keränen et al. |
| 2011/0009957 A1 | 1/2011 | Langberg et al. |
| 2011/0011917 A1 | 1/2011 | Loulmet |
| 2011/0015722 A1 | 1/2011 | Hauser et al. |
| 2011/0022164 A1 | 1/2011 | Quinn et al. |
| 2011/0022166 A1 | 1/2011 | Dahlgren et al. |
| 2011/0060407 A1 | 3/2011 | Ketai et al. |
| 2011/0066234 A1 | 3/2011 | Gordon et al. |
| 2011/0092988 A1 | 4/2011 | Cohen et al. |
| 2011/0093063 A1 | 4/2011 | Schreck |
| 2011/0106106 A1 | 5/2011 | Meier et al. |
| 2011/0106117 A1 | 5/2011 | Mathis et al. |
| 2011/0144743 A1 | 6/2011 | Lattouf |
| 2011/0172754 A1 | 7/2011 | Starksen et al. |
| 2011/0207996 A1 | 8/2011 | Starksen |
| 2011/0213387 A1 | 9/2011 | Nguyen et al. |
| 2011/0224784 A1 | 9/2011 | Quinn |
| 2011/0230961 A1 | 9/2011 | Langer et al. |
| 2011/0230962 A1 | 9/2011 | Moaddeb et al. |
| 2011/0251684 A1 | 10/2011 | Rahdert et al. |
| 2011/0257740 A1 | 10/2011 | Shaoulian et al. |
| 2011/0257741 A1 | 10/2011 | Moaddeb et al. |
| 2011/0264208 A1 | 10/2011 | Duffy et al. |
| 2012/0010461 A1 | 1/2012 | Goldfarb et al. |
| 2012/0041548 A1 | 2/2012 | Crabtree |
| 2012/0053680 A1 | 3/2012 | Bolling et al. |
| 2012/0065464 A1 | 3/2012 | Ellis et al. |
| 2012/0095552 A1 | 4/2012 | Spence et al. |
| 2012/0101442 A1 | 4/2012 | Legaspi et al. |
| 2012/0109288 A1 | 5/2012 | Bolling |
| 2012/0109289 A1 | 5/2012 | Bolling |
| 2012/0123532 A1 | 5/2012 | Mathis |
| 2012/0136433 A1 | 5/2012 | Marmureanu et al. |
| 2012/0158020 A1 | 6/2012 | Crockett et al. |
| 2012/0179184 A1 | 7/2012 | Orlov |
| 2012/0185040 A1 | 7/2012 | Rahdert et al. |
| 2012/0203072 A1 | 8/2012 | Lattouf et al. |
| 2012/0209376 A1 | 8/2012 | Hauser et al. |
| 2012/0209379 A1 | 8/2012 | Shaolian et al. |
| 2012/0215305 A1 | 8/2012 | Le et al. |
| 2012/0221101 A1 | 8/2012 | Moaddeb et al. |
| 2012/0271331 A1 | 10/2012 | To et al. |
| 2012/0310331 A1 | 12/2012 | Eigler et al. |
| 2012/0323314 A1 | 12/2012 | Callas et al. |
| 2013/0006352 A1 | 1/2013 | Yaron |
| 2013/0035757 A1 | 2/2013 | Zentgraf et al. |
| 2013/0110230 A1 | 5/2013 | Solem |
| 2013/0116776 A1 | 5/2013 | Gross et al. |
| 2013/0123913 A1 | 5/2013 | Kuehn |
| 2013/0131791 A1 | 5/2013 | Hlavka et al. |
| 2013/0253639 A1 | 9/2013 | Alkhatib |
| 2013/0253641 A1 | 9/2013 | Lattouf |
| 2013/0282059 A1 | 10/2013 | Ketai et al. |
| 2013/0304093 A1 | 11/2013 | Serina et al. |
| 2013/0304197 A1 | 11/2013 | Buchbinder et al. |
| 2014/0039607 A1 | 2/2014 | Kovach |
| 2014/0066693 A1 | 3/2014 | Goldfarb et al. |
| 2014/0067048 A1 | 3/2014 | Chau et al. |
| 2014/0088693 A1 | 3/2014 | Seguin et al. |
| 2014/0135799 A1 | 5/2014 | Henderson |
| 2014/0148849 A1 | 5/2014 | Serina et al. |
| 2014/0155783 A1 | 6/2014 | Starksen et al. |
| 2014/0172084 A1 | 6/2014 | Callas et al. |
| 2014/0188108 A1 | 7/2014 | Goodine et al. |
| 2014/0207154 A1 | 7/2014 | Bielefeld et al. |
| 2014/0207161 A1 | 7/2014 | Dell et al. |
| 2014/0222138 A1 | 8/2014 | Machold et al. |
| 2014/0228871 A1 | 8/2014 | Cohen et al. |
| 2014/0243860 A1 | 8/2014 | Morris et al. |
| 2014/0243894 A1 | 8/2014 | Groothuis et al. |
| 2014/0243963 A1 | 8/2014 | Sheps et al. |
| 2014/0257341 A1 | 9/2014 | Eidenschink et al. |
| 2014/0275757 A1 | 9/2014 | Goodwin et al. |
| 2014/0276648 A1 | 9/2014 | Hammer et al. |
| 2014/0276971 A1 | 9/2014 | Kovach |
| 2014/0276979 A1 | 9/2014 | Sauer et al. |
| 2014/0309661 A1 | 10/2014 | Sheps et al. |
| 2014/0336756 A1 | 11/2014 | Lee et al. |
| 2014/0364875 A1 | 12/2014 | Zentgraf |
| 2014/0371843 A1 | 12/2014 | Wilson et al. |
| 2014/0379002 A1 | 12/2014 | Morris et al. |
| 2014/0379006 A1 | 12/2014 | Sutherland et al. |
| 2014/0379074 A1 | 12/2014 | Spence et al. |
| 2015/0018940 A1 | 1/2015 | Quill et al. |
| 2015/0018941 A1 | 1/2015 | Lee et al. |
| 2015/0032127 A1 | 1/2015 | Gammie et al. |
| 2015/0038988 A1 | 2/2015 | Tegels et al. |

(56) References Cited

U.S. PATENT DOCUMENTS

| | | |
|---|---|---|
| 2015/0045815 A1 | 2/2015 | Eidenschink |
| 2015/0051697 A1 | 2/2015 | Spence et al. |
| 2015/0057682 A1 | 2/2015 | Kovach |
| 2015/0066138 A1 | 3/2015 | Alexander et al. |
| 2015/0073547 A1 | 3/2015 | Eliasen et al. |
| 2015/0105804 A1 | 4/2015 | Dell et al. |
| 2015/0105855 A1 | 4/2015 | Cabiri et al. |
| 2015/0112432 A1 | 4/2015 | Reich et al. |
| 2015/0119981 A1 | 4/2015 | Khairkhahan et al. |
| 2015/0127091 A1 | 5/2015 | Cecere et al. |
| 2015/0133999 A1 | 5/2015 | Robinson et al. |
| 2015/0134050 A1 | 5/2015 | Solem et al. |
| 2015/0134053 A1 | 5/2015 | Morris et al. |
| 2015/0134055 A1 | 5/2015 | Spence et al. |
| 2015/0134057 A1 | 5/2015 | Rourke et al. |
| 2015/0142105 A1 | 5/2015 | Bolling et al. |
| 2015/0157459 A1 | 6/2015 | Macoviak et al. |
| 2015/0164639 A1 | 6/2015 | Starksen et al. |
| 2015/0173740 A1 | 6/2015 | Sugimoto et al. |
| 2015/0173900 A1 | 6/2015 | Hauser et al. |
| 2015/0182223 A1 | 7/2015 | Ketai et al. |
| 2015/0223793 A1 | 8/2015 | Goldfarb et al. |
| 2015/0272586 A1 | 10/2015 | Herman et al. |
| 2015/0272734 A1 | 10/2015 | Sheps et al. |
| 2015/0297212 A1 | 10/2015 | Reich et al. |
| 2015/0313713 A1 | 11/2015 | Zentgraf et al. |
| 2015/0335430 A1 | 11/2015 | Loulmet et al. |
| 2015/0366556 A1 | 12/2015 | Khairkhahan et al. |
| 2015/0366666 A1 | 12/2015 | Khairkhahan et al. |
| 2016/0008132 A1 | 1/2016 | Cabiri et al. |
| 2016/0015515 A1 | 1/2016 | Lashinski et al. |
| 2016/0015517 A1 | 1/2016 | Sutherland et al. |
| 2016/0022419 A1 | 1/2016 | Yellin et al. |
| 2016/0038285 A1 | 2/2016 | Glenn et al. |
| 2016/0038286 A1 | 2/2016 | Yellin et al. |
| 2016/0058557 A1 | 3/2016 | Reich et al. |
| 2016/0067043 A1 | 3/2016 | Machold et al. |
| 2016/0106420 A1 | 4/2016 | Foerster et al. |
| 2016/0113762 A1 | 4/2016 | Clague et al. |
| 2016/0113767 A1 | 4/2016 | Miller et al. |
| 2016/0120642 A1 | 5/2016 | Shaolian et al. |
| 2016/0143737 A1 | 5/2016 | Zentgraf et al. |
| 2016/0174979 A1 | 6/2016 | Wei |
| 2016/0192925 A1 | 7/2016 | Bachman |
| 2016/0242909 A1 | 8/2016 | Ketai et al. |
| 2016/0262887 A1 | 9/2016 | Chang et al. |
| 2016/0287387 A1 | 10/2016 | Wei |
| 2016/0354082 A1 | 12/2016 | Oz et al. |
| 2016/0374812 A1 | 12/2016 | Machold et al. |
| 2017/0007405 A1 | 1/2017 | Griffin et al. |
| 2017/0020521 A1 | 1/2017 | Krone et al. |
| 2017/0042546 A1 | 2/2017 | Goldfarb et al. |
| 2017/0049455 A1 | 2/2017 | Seguin |
| 2017/0055969 A1 | 3/2017 | Machold et al. |
| 2017/0143330 A1 | 5/2017 | Basude et al. |
| 2017/0189013 A1 | 7/2017 | Morris et al. |
| 2017/0202554 A1 | 7/2017 | Eidenschink |
| 2018/0008404 A1 | 1/2018 | Tamir |
| 2020/0330229 A1 | 10/2020 | Serraf et al. |

OTHER PUBLICATIONS

NPL1 and FP1-FP3 can be found in the parent application.

* cited by examiner

PROLAPSE PREVENTION DEVICE AND METHODS OF USE THEREOF

CROSS-REFERENCE TO RELATED APPLICATIONS

This application is a divisional of U.S. application Ser. No. 17/674,341, filed Feb. 17, 2022, now allowed, which is a continuation of U.S. application Ser. No. 16/352,976, filed on Mar. 14, 2019, now U.S. Pat. No. 11,285,003, which claims the benefit of U.S. Provisional Patent Application Ser. No. 62/645,307, filed Mar. 20, 2018, each of which is hereby incorporated by reference in its entirety for all purposes.

FIELD OF THE INVENTION

The present technology relates generally to devices for repairing a valve suffering from regurgitation, and associated systems and methods.

BACKGROUND OF THE INVENTION

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs to the remaining body. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

The mitral valve, also known as the bicuspid or left atrioventricular valve, is a dual flap valve located between the left atrium and the left ventricle. The mitral valve serves to direct oxygenated blood from the lungs through the left side of the heart and into the aorta for distribution to the body. As with other valves of the heart, the mitral valve is a passive structure in that does not itself expend any energy and does not perform any active contractile function. The mitral valve includes two moveable leaflets, an anterior leaflet and a posterior leaflet, that each open and close in response to differential pressures on either side of the valve. Ideally, the leaflets move apart from each other when the valve is in an open configuration and meet or "coapt" when the valve is in a closed configuration.

Diseases associated with heart valves, such as those caused by damage or a defect, can include stenosis and valvular insufficiency or regurgitation. These diseases can occur individually or concomitantly in the same valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

In particular, a large portion or percentage of degenerative regurgitation in a mitral valve is caused by a prolapsed posterior mitral leaflet. This can be caused by weakening or separation of the chordae attached to the posterior leaflet. In such cases, when the mitral valve is in the closed configuration, the posterior mitral leaflet billows or bulges like a sail or a parachute into the left atrium, causing the posterior leaflet to not fully coapt with the anterior mitral leaflet.

Currently, treatment options for the repair of a prolapsing leaflet includes re-sectioning of the prolapsed tissue, chordae repair, foldoplasty, annuloplasty, placement of a new valve, or attachment of a clip to couple a free end of the prolapsing leaflet to a free end of a non-prolapsing leaflet. However, these solutions have significant drawbacks in terms of efficacy, safety or likelihood of complications, invasiveness, reduction in the cross-sectional area for blood flow through the valve, and the availability of the valve for future treatments.

Accordingly, there is a need for devices that can repair a valve suffering from regurgitation due to a prolapsing leaflet more easily, with greater efficacy and fewer complications.

BRIEF SUMMARY OF THE INVENTION

Embodiments hereof are directed to an implantable prosthesis, referred to herein as a prolapse prevention device, for treating a regurgitating heart valve. In an embodiment, the prolapse prevention device is formed by a continuous wire-like structure having a first end and a second end that opposes the first end, the first end and the second end being disconnected from each other. The continuous wire-like structure of the prolapse prevention device is substantially straight in a delivery configuration. The continuous wire-like structure of the prolapse prevention device in a deployed configuration includes a centering ring configured to seat adjacent to and upstream of an annulus of a heart valve to circumferentially center the prolapse prevention device in situ, a vertical support extending from the centering ring such that an apex thereof is configured to seat against a roof of the atrium in situ, and a leaflet backstop extending radially inward from the centering ring and configured to contact at least a first leaflet of the heart valve in situ to exert a pressure in a downstream direction on the first leaflet to prevent the first leaflet from prolapsing into the atrium.

In another embodiment, the prolapse prevention device is formed by a continuous wire-like structure having a first end and a second end that opposes the first end, the first end and the second end being disconnected from each other. The prolapse prevention device in a deployed configuration includes a centering ring configured to seat adjacent to and upstream of an annulus of a heart valve to circumferentially center the prolapse prevention device in situ. The centering ring is an open ring. The prolapse prevention device in the deployed configuration further includes an inner tail that conforms to an inner surface of the centering ring and is configured to permit the open ring to self-adjust to a size of the annulus of the heart valve. The prolapse prevention device in the deployed configuration further includes a leaflet backstop extending radially inward from the centering ring and configured to contact at least a first leaflet of the heart valve in situ to exert a pressure in a downstream direction on the first leaflet to prevent the first leaflet from prolapsing into the atrium, a vertical support extending from the centering ring in an upstream direction such that an apex thereof is configured to seat against a roof of an atrium in situ, and a retrieval arm extending from the apex of the vertical support in a downstream direction, away from the roof of the atrium.

Embodiments hereof are also directed to methods of treating heart valvular regurgitation with a system including a delivery catheter and a prolapse prevention device. More particularly, the system is percutaneously introduced into a vasculature. The system is delivered through the vasculature to a heart valve with the prolapse prevention device in a delivery configuration. The prolapse prevention device is formed by a continuous wire-like structure having a first end and a second end that opposes the first end, the first end and the second end being disconnected from each other. The continuous wire-like structure is substantially straight when the prolapse prevention device is in the delivery configuration. A distal end of the delivery catheter is positioned adjacent to an annulus of a heart valve. The prolapse prevention device is deployed such that a centering ring of the continuous wire-like structure is seated adjacent to and upstream of the annulus of the heart valve, a vertical support of the continuous wire-like structure extends from the centering ring and an apex thereof is seated against a roof of the atrium, and a leaflet backstop of the continuous wire-like structure is extending radially inward from the centering ring and contacts at least a first leaflet of the heart valve to exert a pressure in a downstream direction on the first leaflet to prevent the first leaflet from prolapsing into the atrium.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a delivery device, delivery system, or delivery catheter are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a system or a device to be implanted into a vessel, such as a device for treating heart valvular regurgitation, are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

The following detailed description is merely exemplary in nature and is not intended to limit the present technology or the application and uses of the present technology. Although the description of embodiments hereof is in the context of treatment of heart valvular regurgitation and particularly in the context of treatment of regurgitation of the mitral valve, the present technology may also be used in any other body passageways where it is deemed useful including other heart valves. Furthermore, there is no intention to be bound by any expressed or implied theory presented in the preceding technical field, background, brief summary or the following detailed description.

Figure 1:
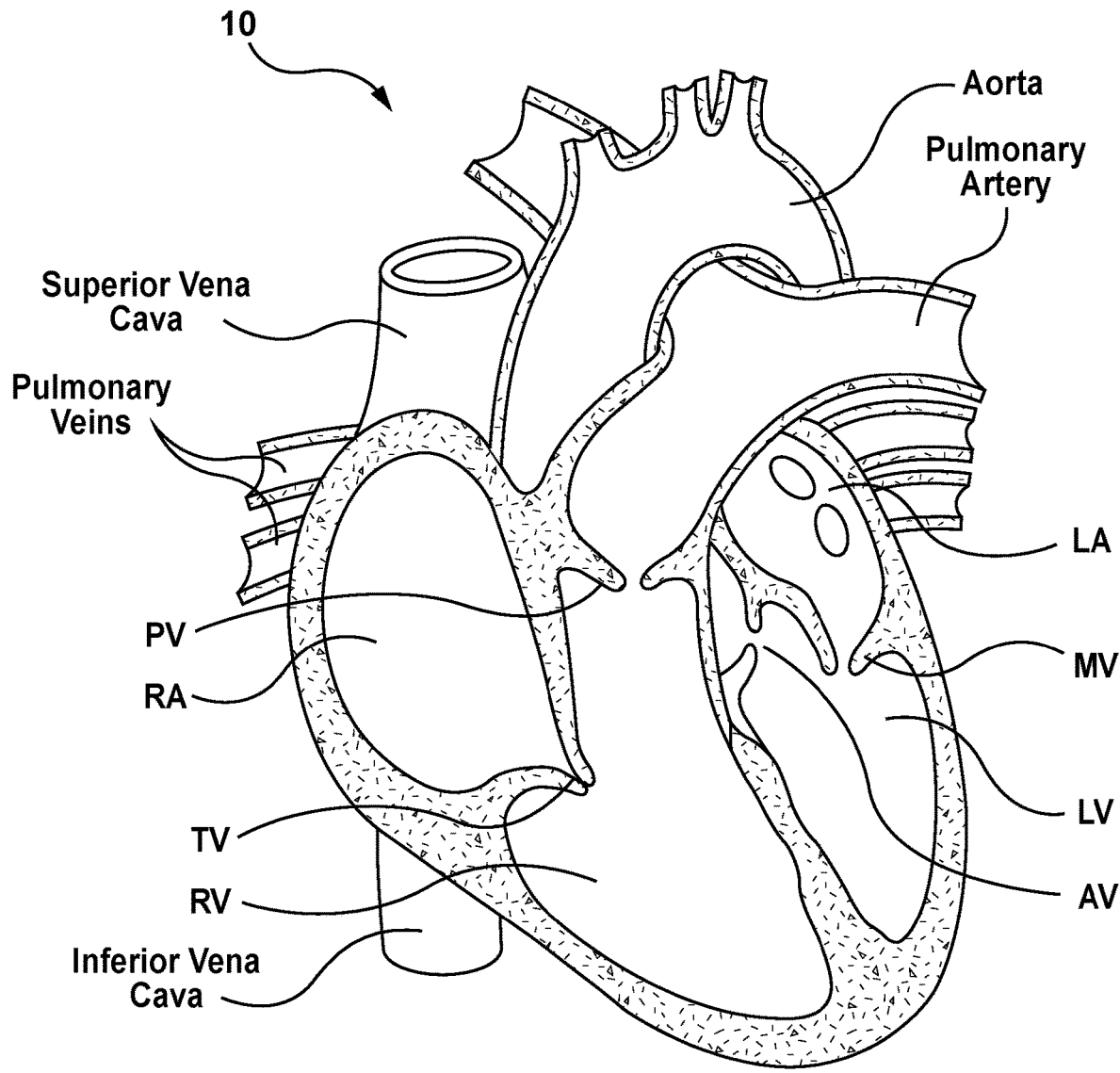
FIG. 1 is a schematic sectional illustration of a mammalian heart having native valve structures.
Figure 2A:
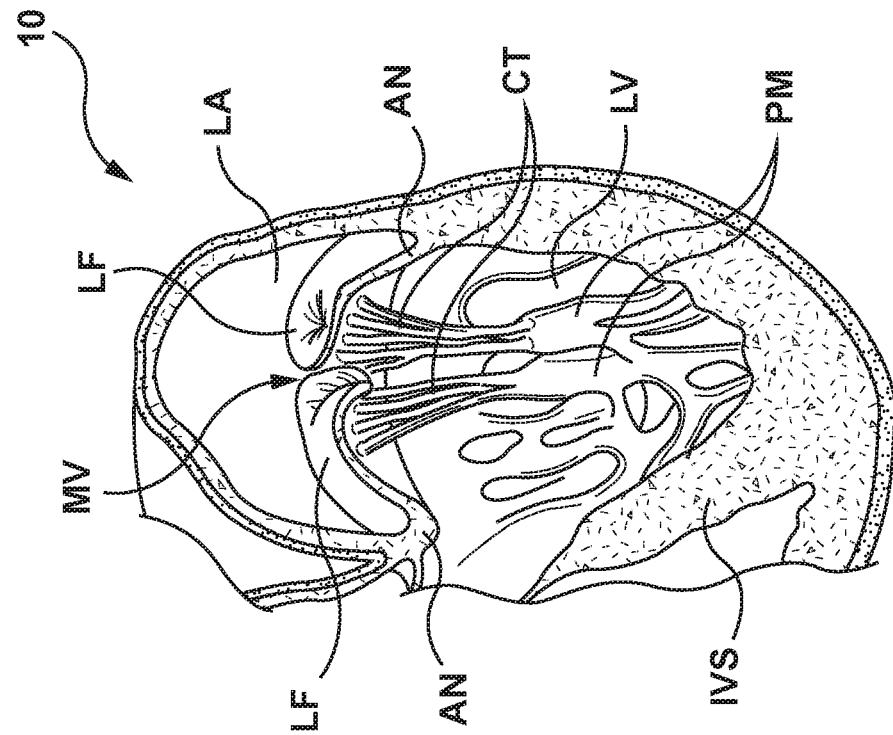
FIG. 2A is a schematic sectional illustration of a left ventricle of a mammalian heart showing anatomical structures and a native mitral valve.
Figure 2B:
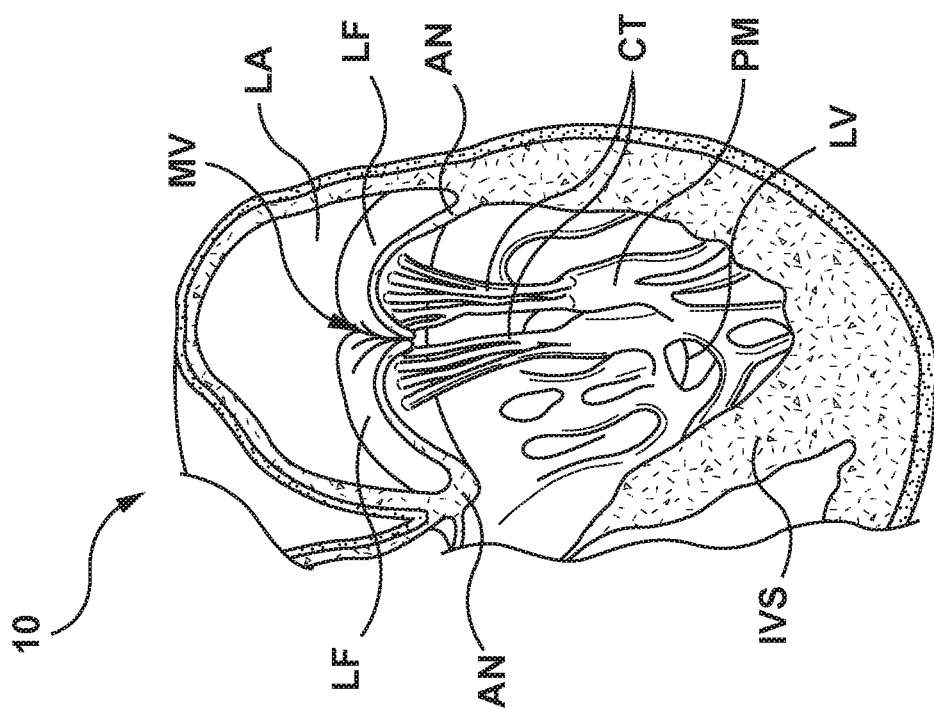
FIG. 2B is a schematic sectional illustration of the left ventricle of a heart having a prolapsed mitral valve in which the leaflets do not sufficiently coapt and which is suitable for repair with a device in accordance with embodiments hereof.
Figure 2C:
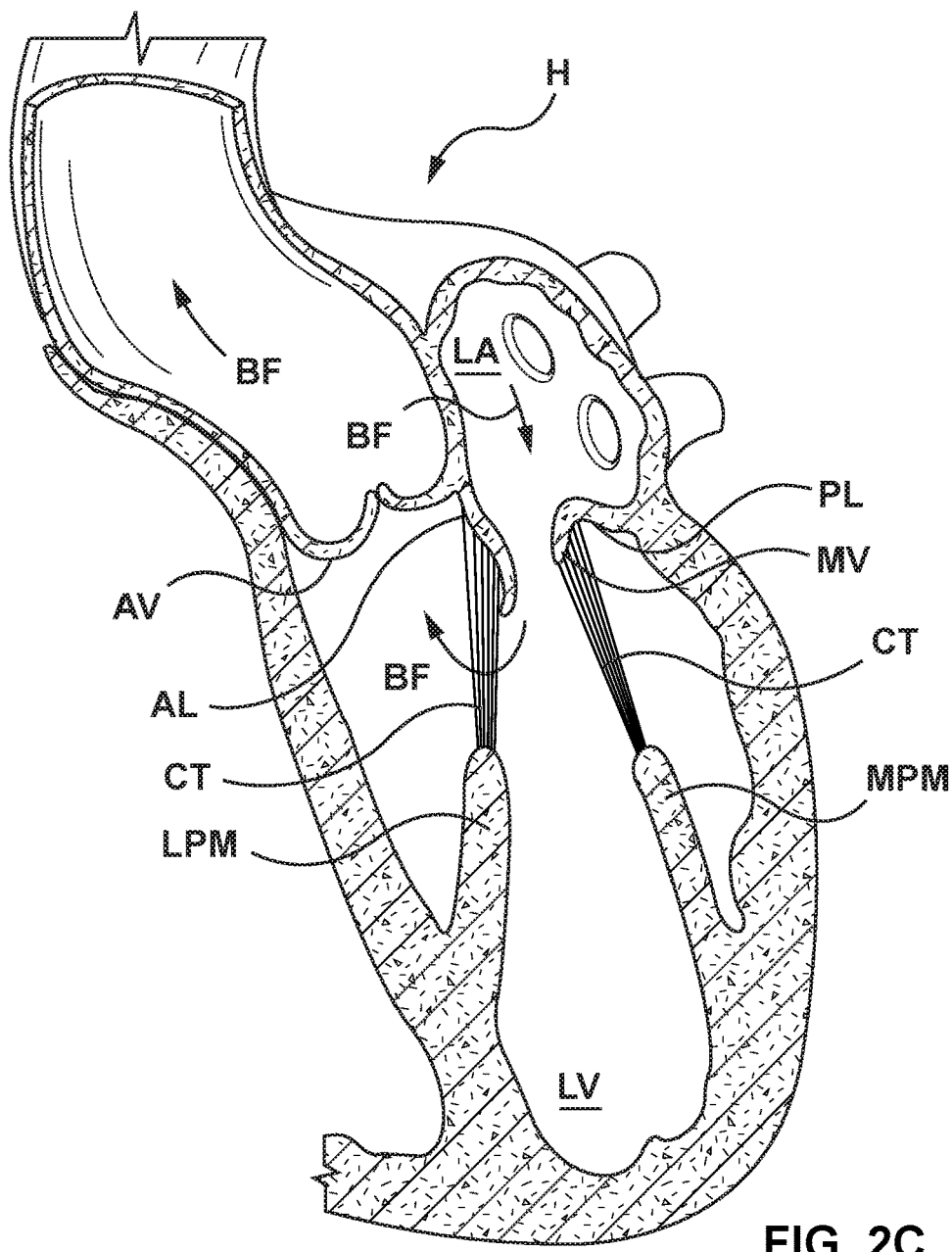
FIG. 2C is a schematic sectional illustration of the left ventricle of FIG. 2B as viewed from a different angle.
Figure 2D:
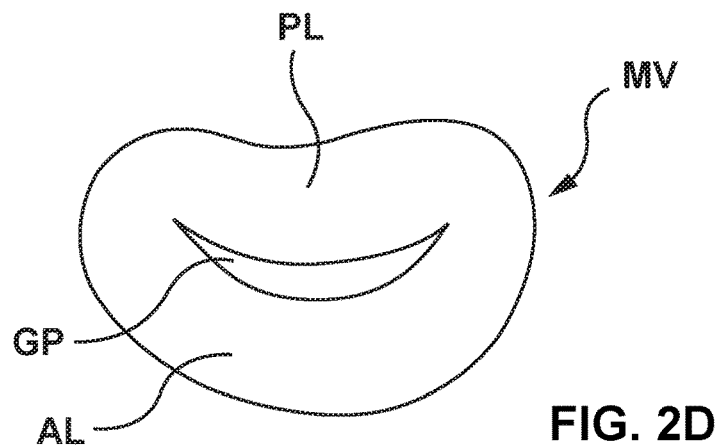
FIG. 2D is a top view illustration of the prolapsed mitral valve of FIG. 2B, wherein the mitral valve is in an open configuration.
Figures 2E, 2F:
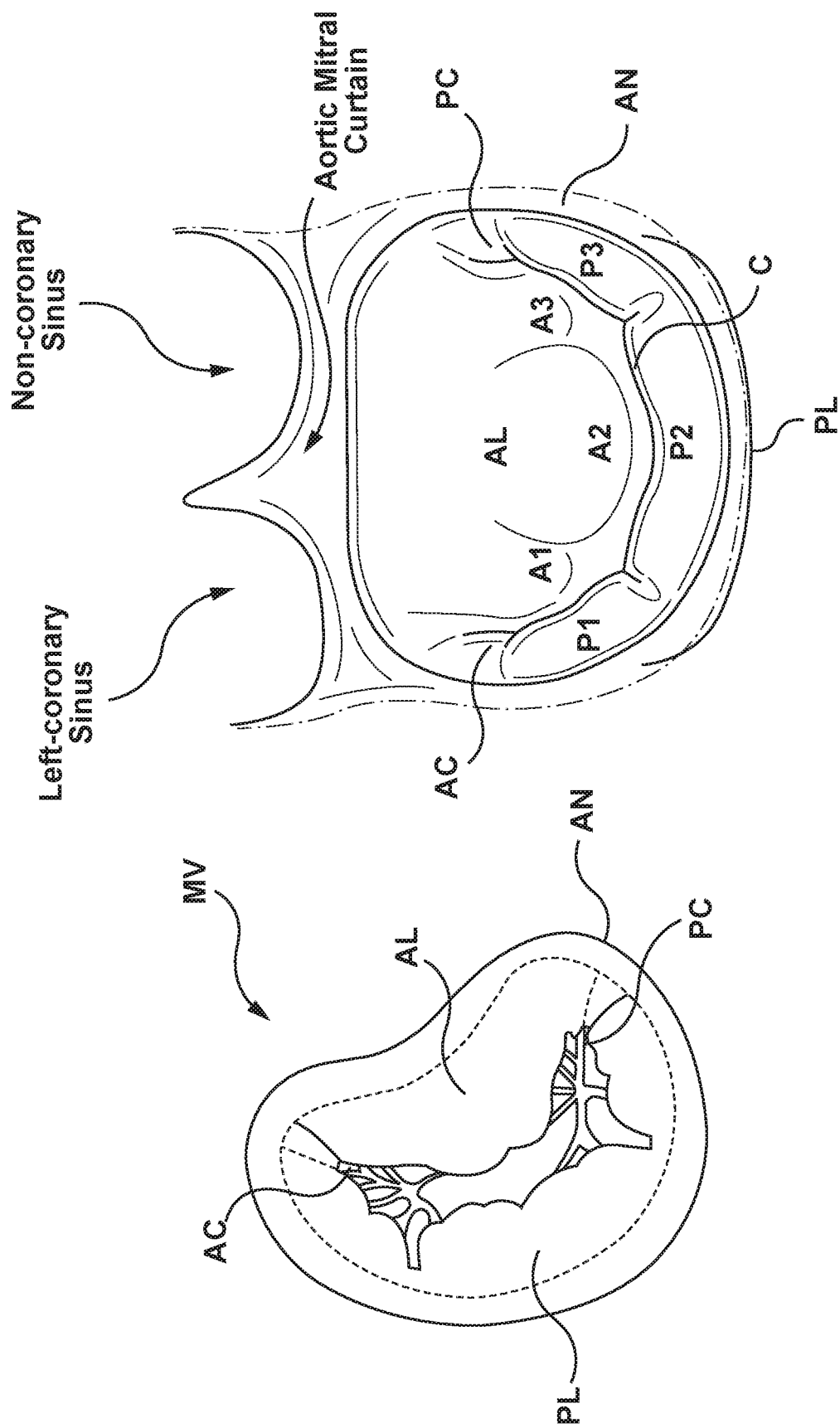
FIG. 2E is a schematic illustration of a superior view a mitral valve isolated from the surrounding heart structures and showing the annulus and native leaflets.
FIG. 2F is a schematic illustration of a superior view a mitral valve, aortic mitral curtain and portions of the aortic valve isolated from the surrounding heart structures and showing regions of the native mitral valve leaflets.

FIGS. 1-2F will now be described to provide contextual information on valve regurgitation. FIG. 1 is a schematic sectional illustration of a mammalian heart 10 that depicts the four heart chambers (right atrium RA, right ventricle RV, left atrium LA, left ventricle LV) and native valve structures (tricuspid valve TV, mitral valve MV, pulmonary valve PV, aortic valve AV). FIG. 2A is a schematic sectional illustration of a left ventricle LV of the heart 10 showing anatomical structures and a native mitral valve MV. Referring to FIGS. 1 and 2A together, the heart 10 comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

In a healthy heart, the leaflets LF of the mitral valve MV meet evenly at the free edges or "coapt" to close and prevent back flow of blood during contraction of the left ventricle LV (FIG. 2A). Referring to FIG. 2A, the leaflets LF attach to the surrounding heart structure via a dense fibrous ring of connective tissue called an annulus AN which is distinct from both the leaflet tissue LF as well as the adjoining muscular tissue of the heart wall. In general, the connective tissue at the annulus AN is more fibrous, tougher and stronger than leaflet tissue. The flexible leaflet tissue of the mitral leaflets LF are connected to papillary muscles PM, which extend upwardly from the lower wall of the left ventricle LV and the interventricular septum IVS, via branching tendons called chordae tendinae CT. In a heart 10 having a prolapsed mitral valve MV in which the leaflets LF do not sufficiently coapt or meet, as shown in FIGS. 2B-2D, leakage from the left atrium LA into the left ventricle LV will occur through a gap GP. Several structural defects can cause the mitral leaflets LF to prolapse such that regurgitation occurs, including ruptured chordae tendinac CT, impairment of papillary muscles PM (e.g., due to ischemic heart disease), and enlargement of the heart and/or mitral valve annulus AN (e.g., cardiomyopathy).

FIG. 2E is a superior view of a mitral valve MV isolated from the surrounding heart structures and further illustrating the shape and relative sizes of the mitral valve leaflets AL, PL and annulus AN. FIG. 2F is a schematic illustration of a superior view a mitral valve MV, aortic mitral curtain and portions of the aortic valve AV isolated from the surrounding heart structures and showing regions of the native mitral valve leaflets AL, PL. With reference to FIGS. 2E and 2F together, the mitral valve MV includes an anterior leaflet AL with segments or scallops A1, A2, and A3 that meet and oppose respective segments or scallops P1, P2 and P3 of a posterior leaflet PL at a coaptation line C (FIG. 2F) when closed. FIGS. 2E and 2F together further illustrate the shape and relative sizes of the leaflets AL, PL of the mitral valve. As shown, the mitral valve MV generally has a "D" or kidney-like shape and the line of coaptation C is curved or C-shaped, thereby defining a relatively large anterior leaflet AL and substantially smaller posterior leaflet PL. Both leaflets appear generally crescent-shaped from the superior or atrial side, with the anterior leaflet AL being substantially wider in the middle of the valve at the A2 segment thereof than the posterior leaflet at the P2 segment thereof (e.g., comparing segments A2 and P2, FIG. 2F). As illustrated in FIGS. 2E and 2F, at the opposing ends of the line of coaptation C, the leaflets join together at corners called the anterolateral commissure AC and posteromedial commissure PC, respectively. When the anterior leaflet AL and posterior leaflet PL fail to meet (FIG. 2E), regurgitation between the leaflets AL, PL or at commissures AC, PC at the corners between the leaflets can occur.

With continued reference to FIGS. 2E and 2F, the mitral valve annulus AN is a fibrotic ring that consists of an anterior part and a posterior part. The aortic-mitral curtain (FIG. 2F) is a fibrous structure that connects the anterior mitral annulus AN intimately with the aortic valve annulus (at the level of the left and non-coronary cusps or sinuses). The posterior part of the mitral annulus AN is not reinforced by other structures of the heart and is rather discontinuous (making it prone to dilatation). The leaflets AL, PL and the annulus AN are comprised of different types of cardiac tissue having varying strength, toughness, fibrosity, and flexibility. Furthermore, the mitral valve MV may also comprise a region of tissue interconnecting each leaflet to the annulus AN (indicated at dashed line in FIG. 2E).

A person of ordinary skill in the art will recognize that the dimensions and physiology of the patient may vary among patients, and although some patients may comprise differing physiology, the teachings as described herein can be adapted for use by many patients having various conditions, dimensions and shapes of the mitral valve. For example, research suggests that patients may have a long dimension across the annulus and a short dimension across the annulus with or without well-defined peak and valley portions, and the methods and devices as described herein can be configured accordingly.

Embodiments of devices and associated methods of use for treating valvular regurgitation by repairing and/or preventing at least one leaflet of a native heart valve from prolapsing to reduce or eliminate valvular regurgitation in accordance with embodiments hereof are described with reference to FIGS. 3-17. As will be described in more detail herein, the prolapse prevention devices described herein are pre-set or pre-shaped wires or wire-like structures that may be straightened into an extremely low profile for percutaneous transcatheter delivery and deployment into the atrial space. When deployed or expanded within an atrium of a heart to their pre-set or pre-shaped configuration, the prolapse prevention devices described herein include a circumferential centering feature as well as a longitudinal positioning feature so that a leaflet backstop portion thereof is accurately positioned to limit or restrain motion of a prolapsing leaflet into the atrium of a heart. The prolapse prevention devices described herein are self-adjustable and tunable to avoid or minimize abrasion of the atrium and/or native valve leaflets, and the minimal material thereof avoids obstructing other anatomic structures branching from the atrium such as the pulmonary veins. Further, as will be explained in more detail herein, positioning of the prolapse prevention devices described herein may be evaluated before release thereof from a delivery catheter and may be recaptured and re-deployed if adjustments to the positioning are desired. Further advantages of the prolapse prevention devices will be described in more detail herein with respect to the figures. It will be appreciated that specific elements, substructures, uses, advantages, and/or other aspects of the embodiments described herein and with reference to FIGS. 3-17 can be suitably interchanged, substituted or otherwise configured with one another in accordance with additional embodiments described herein.

Figure 3:
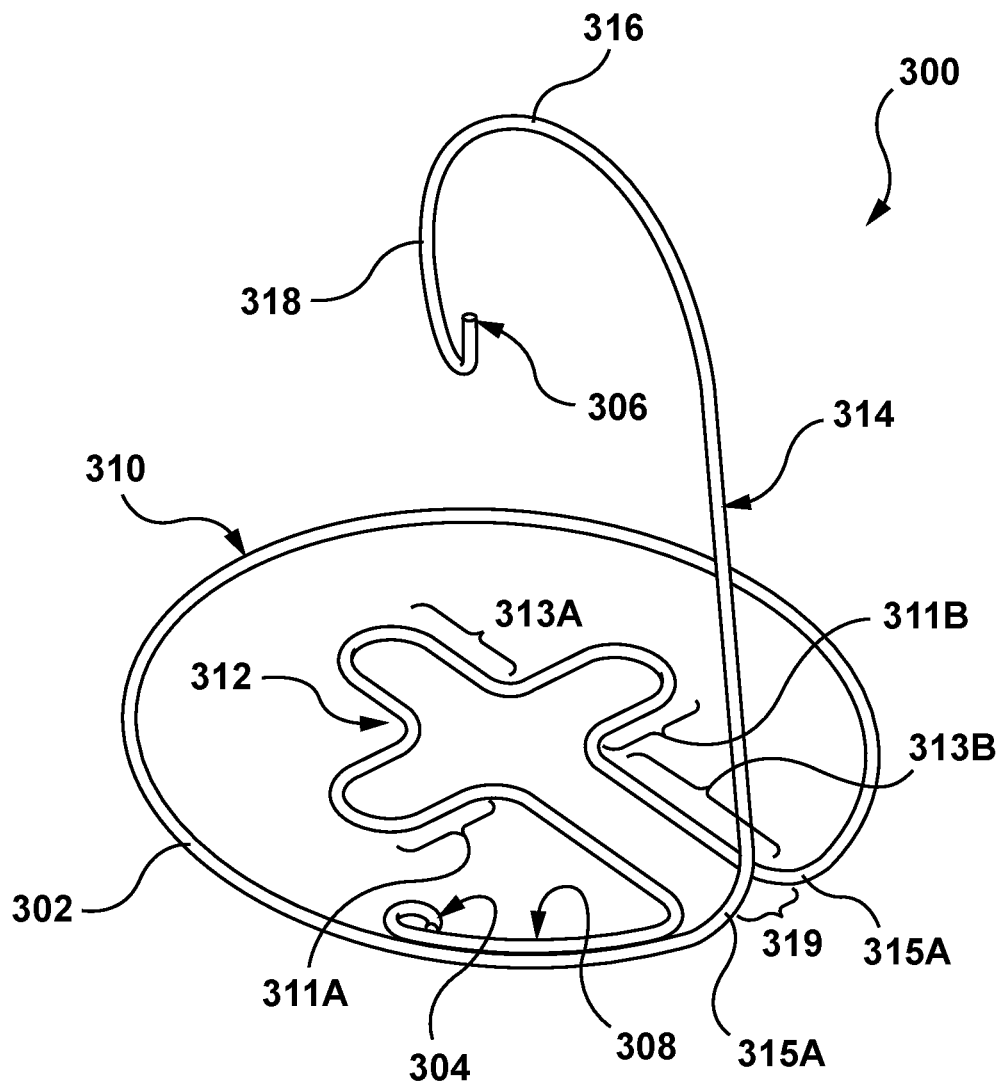
FIG. 3 is a perspective illustration of a prolapse prevention device for treating heart valvular regurgitation in accordance with an embodiment hereof, wherein the prolapse prevention device is shown in its deployed configuration.

Turning to FIG. 3, FIG. 3 is a perspective view of an implantable prosthesis or prolapse prevention device 300 for treating regurgitation of a heart valve due to a prolapsing leaflet. The prolapse prevention device 300 includes a delivery configuration, in which the prolapse prevention device 300 is substantially straightened for percutaneous delivery within a delivery catheter to the treatment site (i.e., to the heart valve) as will be described in more detail herein with respect to FIG. 9, and a deployed configuration which is shown in FIG. 3. When the prolapse prevention device 300 is in the deployed configuration at the site of a heart valve suffering from a prolapsing leaflet and regurgitation, the prolapse prevention device 300 is configured to prevent the leaflet from prolapsing, thereby reducing or eliminating valvular regurgitation as described below.

The prolapse prevention device 300 is an implantable prosthesis formed by a wire or wire-like structure 302 having a first end 304 and a second end 306 that opposes the first end 304. The first end 304 and the second end 306 are disconnected, detached, or otherwise separated from each other. In an embodiment, as described in more detail herein, the first end 304 and the second end 306 are formed in the shape of a hook to permit subsequent retrieval of the prolapse prevention device 300. The wire-like structure 302 is a continuous strand or component that is formed from a self-expanding material and is pre-set in its deployed configuration shown in FIG. 3. Stated another way, in order to transform or self-expand between the delivery configuration and the deployed configuration, the prolapse prevention device 300 is formed from a resilient or shape memory material, such as a nickel titanium alloy (e.g., nitinol), that has a mechanical memory to return to the deployed or expanded configuration. Suitable resilient or shape memory materials include stainless steel, a pseudo-elastic metal such as nickel titanium alloy or nitinol, a so-called super alloy, which may have a base metal of nickel, cobalt, chromium, or other metal, MP35N spring wire, an acetal copolymer, or a polymeric material having shape memory characteristics. The material of the wire-like structure 302 has an inherent spring restorative force or mechanical memory to return to its original pre-set or preformed shape after being loaded. "Resilient" and "resilience" as used herein to refer to a material that is capable of recovering an original pre-set shape or form after being elastically stretched, deformed, compressed, or the like. Mechanical memory may be imparted to the wire-like structure 302 that forms the prolapse prevention device 300 by thermal treatment to achieve a spring temper in stainless steel, for example, or to set a shape memory in a susceptible metal alloy, such as nitinol. For example, the wire-like structure 302 of the prolapse prevention device 300 may be shape-set into the closed configuration using an oven set to an appropriate temperature for the material, by e.g., approximately 525° C. for nitinol although the temperature will vary depending on the material of the wire-like structure 302.

In various embodiments in accordance herewith, the wire-like structure 302 may be solid or hollow and have a circular cross-section. By minimizing the cross-section of the wire-like structure 302, the amount of foreign material implanted in the body and the interruption or footprint of the implant relative to blood flow is minimized to avoid thrombosis. In one embodiment, the wire-like structure 302 has a diameter less than 0.10 inches. In one embodiment, the wire-like structure 302 has a diameter between 0.006 inches-0.040 inches. In another embodiment, the cross-section of the wire-like structure 302 may be an oval, square, rectangular, or any other suitable shape, as well as combinations thereof in which the cross-section of the wire-like structure changes along the length thereof.

The wire-like structure 302 is shaped to include an inner tail 308, a centering ring 310, a leaflet backstop 312, a vertical support 314 having an apex 316, and a retrieval arm 318. Although separately described, such portions or sections of the wire-like support 302 are integrally formed such that the prolapse prevention device 300 is a unitary structure formed from a single piece of material. The portions or sections of the wire-like support 302 are separately described such that the shape, structure, function and advantages thereof are clear. The portions or sections of the wire-like support 302 collectively enable or configure the prolapse prevention device 300 in the deployed configuration to prevent at least a first leaflet of the heart valve from prolapsing. More particularly, the prolapse prevention device 300 in the deployed configuration causes a prolapsing first leaflet to coapt with a second leaflet of the heart valve when the heart valve is in a closed configuration and thereby prevents and/or repairs valvular regurgitation.

Each integral portion or section of the wire-like support 302 will now be described in more detail in turn with respect to FIG. 3. The leaflet backstop 312 of the prolapse prevention device 300 extends radially inward from the centering ring 310 and is configured to contact at least a first leaflet of a native heart valve in situ. Along the length of the wire-like structure 302, the leaflet backstop 312 integrally extends between the inner tail 308 and the centering ring 310. More particularly, when positioned in situ, the leaflet backstop 312 extends radially inward from the centering ring 310 towards a free or unattached edge of a prolapsing native leaflet. The prolapse prevention device 300 is shaped to position or dispose the leaflet backstop 312 directly above (i.e., in an upstream direction) the prolapsing native leaflet in situ such that at least the prolapsing native leaflet is limited, restrained, or otherwise prevented from prolapsing into the atrium. Although embodiments herein describe that the leaflet backstop 312 is configured to contact at least a first leaflet of a native heart valve, or at least a prolapsing leaflet of a native heart valve, the leaflet backstop 312 may be sized and configured to further contact a second or non-prolapsing leaflet of the native heart valve.

Figure 4:
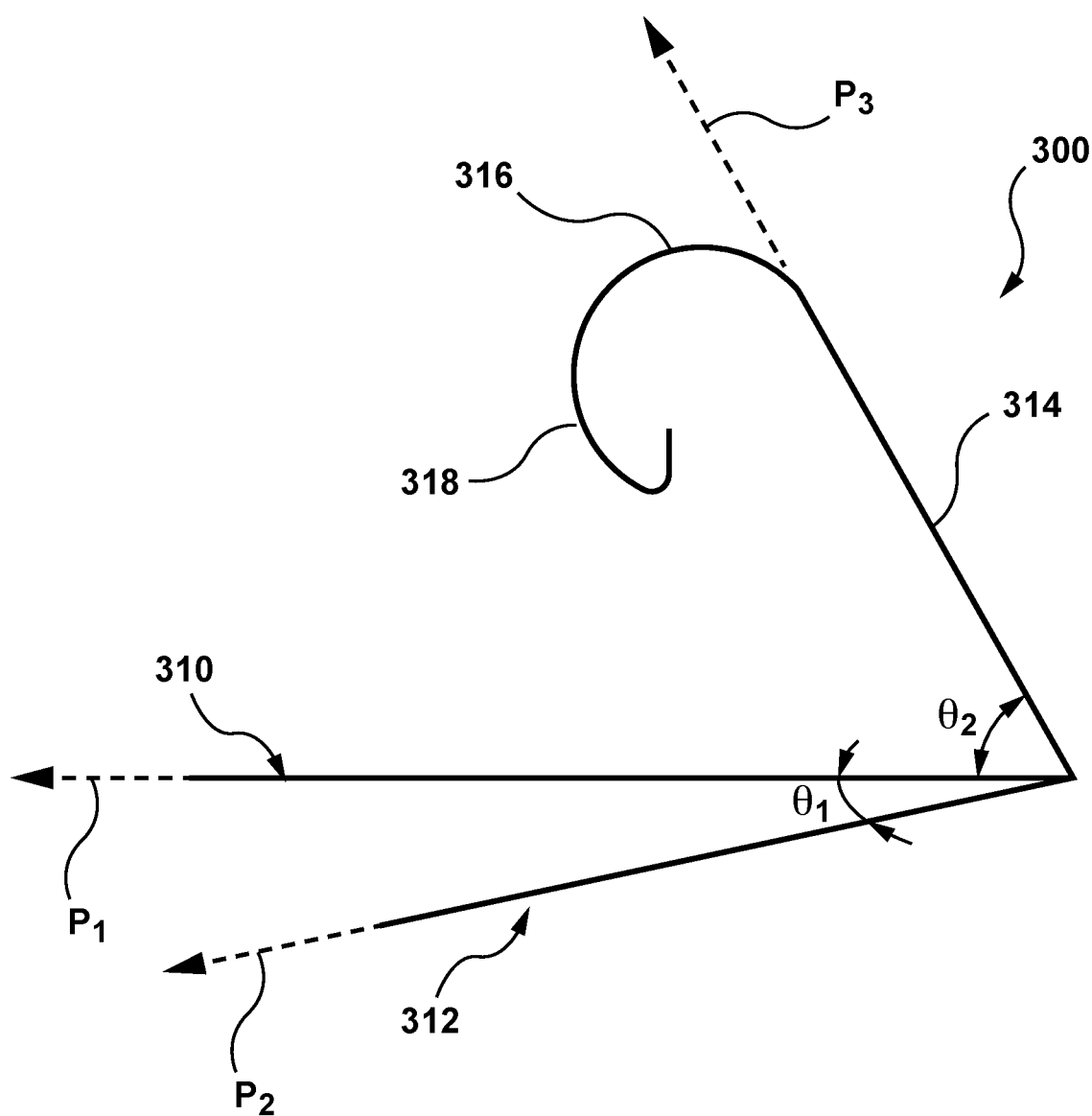
FIG. 4 is a side view of the prolapse prevention device of FIG. 3.

As best shown in the side view of FIG. 4, in an embodiment hereof, the leaflet backstop 312 extends at a downward (i.e., in a downstream direction) angle from the centering ring 310 to ensure downward pressure is exerted onto at least the prolapsing native leaflet. Stated another way, the centering ring 310 lies within or along a first plane $P_1$ and the leaflet backstop 312 lies within or along a second plane $P_2$ when the prolapse prevention device 300 is in the deployed configuration. As shown in FIG. 4, an angle $\Theta_1$ is formed between the first plane $P_1$ and the second plane $P_2$. In an embodiment, angle $\Theta_1$ is between fifteen degrees and sixty degrees, and in another embodiment, angle $\Theta_1$ is between zero and twenty degrees.

In the embodiment of FIG. 3, the leaflet backstop 312 has a cross or "t" shaped configuration. More particularly, the cross configuration of leaflet backstop 312 includes a first stem or leg 313A, a second stem or leg 313B, a first lobe or arm 311A, and a second lobe or arm 311B. The first leg 313A and the second leg 313B are aligned and parallel to each other. In the embodiment of FIG. 3, the second leg 313B is longer than the first leg 313A. However, the second leg 313B may be shorter than the first leg 313A or may be the same length as the first leg 313A. The first arm 311A and the second arm 311B are aligned and parallel to each other. In the embodiment of FIG. 3, the first arm 311A and the second arm 311B are the same length. However, the first arm 311A and the second arm 311B may be different lengths. The first leg 313A and the second leg 313B extend perpendicular to the first arm 311A and the second arm 311B in order to form the cross configuration of the leaflet backstop 312. The cross configuration covers a wide or large amount of surface area, thus ensuring sufficient downward pressure is exerted onto a native valve leaflet by the leaflet backstop 312 and making it easier to correctly position the prolapse prevention device 300. Although the cross or "t" shaped configuration of the leaflet backstop 312 illustrated in FIG. 3 includes only a single pair of lobes or arms (i.e., the first arm 311A and the second arm 311B) extending radially outwardly from the first leg 313A and the second leg 313B, in another embodiment hereof (not shown) the leaflet backstop may include two or more pairs of lobes or arms extending radially outwardly from the first leg 313A and the second leg 313B.

The centering ring 310 is a circumferential centering feature of the prolapse prevention device 300. More particularly, the centering ring 310 is configured to seat just above, or adjacent to and upstream of, an annulus of a heart valve to circumferentially center the prolapse prevention device 300 with respect to the annulus of the heart valve in situ. As used herein, "adjacent to and upstream of" or "just above" an annulus of a heart valve means that the centering ring is disposed directly above a plane of the annulus of the native valve, including disposition at or on a level of an upper surface of the annulus or other superior levels of the valve. The centering ring 310 exerts radial pressure onto the surrounding native tissue to anchor the prolapse prevention device 300 in place. While the centering ring 310 of FIG. 3 is shown with a specific shape, i.e., circular, this is by way of example and not limitation, and it will be understood that the centering ring 310 may assume any number of alternative shapes suitable to treat valvular regurgitation. The shape of the centering ring 310 may be selected based upon the shape of the native anatomy and/or desired anchoring positions. While shown as circular, the centering ring 310 may have other shapes including but not limited to an ellipse, an oval, D-shaped, or any other shape suitable for the purposes described herein. Further, the resilient nature of the wire-like structure 302 permits the centering ring 310 to conform to the shape of the surrounding native tissue in situ. Along the length of the wire-like structure 302, the centering ring 310 integrally extends between the leaflet backstop 312 and the vertical support 314.

The inner tail 308 abuts or conforms to an inner surface of the centering ring 310 and permits the centering ring 310 to self-adjust in size to the surrounding native tissue in situ. More particularly, the centering ring 310 is an open ring having a first end 315A and a second end 315B. "Open ring" as used herein means that the centering ring 310 is an annular component in which the first end 315A is not attached to the second end 315B. The open ring structure of the centering ring 310 in combination with the inner tail 308 allows for natural anatomical sizing of the centering ring 310 so that the centering ring 310 may conform to a range of sizes of native anatomies and anchor the prolapse prevention device 300 therein. More particularly, the centering ring 310 of the prolapse prevention device 300 is shown in FIG. 3 with only a relatively small space or gap 319 extending between the first end 315A and the second end 315B thereof. If the prolapse prevention device 300 is deployed within an anatomy requiring the centering ring 310 to have a greater diameter than shown in FIG. 3, the centering ring 310 radially expands such that the diameter thereof increases and the gap 319 widens as the first end 315A of the centering ring 310 moves apart from the second end 315B of the centering ring 310. Further, as the centering ring 310 radially expands, the amount of overlap between the centering ring 310 and the inner tail 308 decreases. When the amount of overlap between the centering ring 310 and the inner tail 308 decreases, at least a portion of the inner tail 308 is uncovered (i.e., is no longer covered by or disposed within the centering ring 310) and thus serves to exert radial pressure onto the surrounding native tissue to anchor the prolapse prevention device 300 in place. Stated another way, the inner tail 308 is a back-up or standby structure that serves to circumferentially center and anchor the prolapse prevention device 300 into place as the centering ring 310 radially expands. Conversely, if the prolapse prevention device 300 is deployed within an anatomy requiring the centering ring 310 to have a smaller diameter, the centering ring 310 radially contracts such that the diameter thereof decreases and the gap 319 shortens as the first end 315A of the centering ring 310 moves closer to the second end 315B of the centering ring 310. In some embodiments, the gap 319 may disappear such that the first end 315A and the second end 315B of the centering ring 310 abut against each other and/or overlap. Since the inner tail 308 is not attached to the inner surface of the centering ring 310, the inner tail 308 and the centering ring 310 essentially slide or move relative to each other to permit expansion or contraction of the centering ring 310, thereby decreasing or increasing the amount of overlap between the centering ring 310 and the inner tail. Along the length of the wire-like structure 302, the inner tail 308 integrally extends between the first end 304 of the wire-like structure 302 and the leaflet backstop 312. The first end 304 of the wire-like structure 302 and the inner tail 308 lie within or along the same plane as the centering ring 310, namely the first plane $P_1$ shown on the side view of FIG. 4, when the prolapse prevention device 300 is in the deployed configuration.

The vertical support 314 is a longitudinal positioning feature of the prolapse prevention device 300. More particularly, the vertical support 314 extends in an upward or upstream direction from the centering ring 310 such that the apex 316 thereof is configured to seat against a roof of the atrium in situ. The vertical support 314 is a longitudinal positioning feature because it braces the wire-like structure 302 against the roof of the atrial wall, thereby seating the leaflet backstop 312 just above, or adjacent to and upstream of, the annulus of a heart valve. Stated another way, the vertical support 314 is configured to longitudinally position the prolapse prevention device 300 within an atrium of the heart such that the leaflet backstop 312 contacts a prolapsing first leaflet of the heart valve when the prolapse prevention device 300 is deployed within the atrium. Collectively, the centering ring 310 and/or the vertical support 314 eliminate or minimize canting of the prolapse prevention device 300, or stated another way, position prolapse prevention device 300 in situ such that the plane $P_1$ (see FIG. 4) of the centering ring 310 is substantially parallel to a plane of the annulus of the native mitral valve MV. Along the length of the wire-like structure 302, the vertical support 314 integrally extends between the centering ring 310 and the retrieval arm 318.

As best shown in the side view of FIG. 4, in an embodiment hereof, the vertical support 314 extends at an angle from the centering ring 310 to minimize obstruction or interference with other anatomic features within the atrium such as the pulmonary veins. Stated another way, the centering ring 310 lies within or along the first plane $P_1$ and the vertical support 314 lies within or along a third plane $P_3$ when the prolapse prevention device 300 is in the deployed configuration. As shown in FIG. 4, an angle $\Theta_2$ is formed between the first plane $P_1$ and the third plane $P_3$. In an embodiment, angle $\Theta_2$ is between forty-five degrees and eighty degrees, and in another embodiment, angle $\Theta_2$ is between eighty degrees and one hundred degrees.

The last integral portion or section of the wire-like structure 302 to be described is the retrieval arm 318. Along the length of the wire-like structure 302, the retrieval arm 318 integrally extends between the vertical support 314 and the second end 306 of the wire-like structure 302. The retrieval arm 318 is the last integral portion or section of the wire-like structure 302 to be deployed in situ, and primarily functions to permit retrieval of the prolapse prevention device 300 after full deployment of the prolapse prevention device 300. Such retrieval of the prolapse prevention device 300 is discussed in more detail below with respect to the method steps illustrated in FIGS. 10-15. The retrieval arm 318 extends in a downward or downstream direction from the apex 316 of the vertical support 314. As shown in FIG. 3, the retrieval arm 318 may be curved or rounded so as to be atraumatic within the atrium.

As described above, the wire-like structure 302 preferably integrally includes the inner tail 308, the centering ring 310, the leaflet backstop 312, the vertical support 314, and the retrieval arm 318 such that the prolapse prevention device 300 is a unitary structure formed from a single piece of material. However, in another embodiment, one or more of the above-described sections or portions of the prolapse prevention device 300 may be formed as a separate component that is subsequently attached to the remaining sections or portions to form the continuous wire-like structure 302 by any suitable manner known in the art such as for example welding, including resistance welding, friction welding, laser welding or another form of welding, soldering, using an adhesive, adding a connecting element there between, or by another mechanical method. For example, in an embodiment hereof, it may be desirable to form the retrieval arm 318 of a radiopaque material to aid in retrieval of the prolapse prevention device 300. The retrieval arm 318 may be formed as a separate component and subsequently attached to the vertical support 314 to form the continuous wire-like structure 302. In another embodiment, the retrieval arm 308 may be formed integrally with the remainder of the wire-like structure 302 and coated with radiopaque material.

Figure 5:
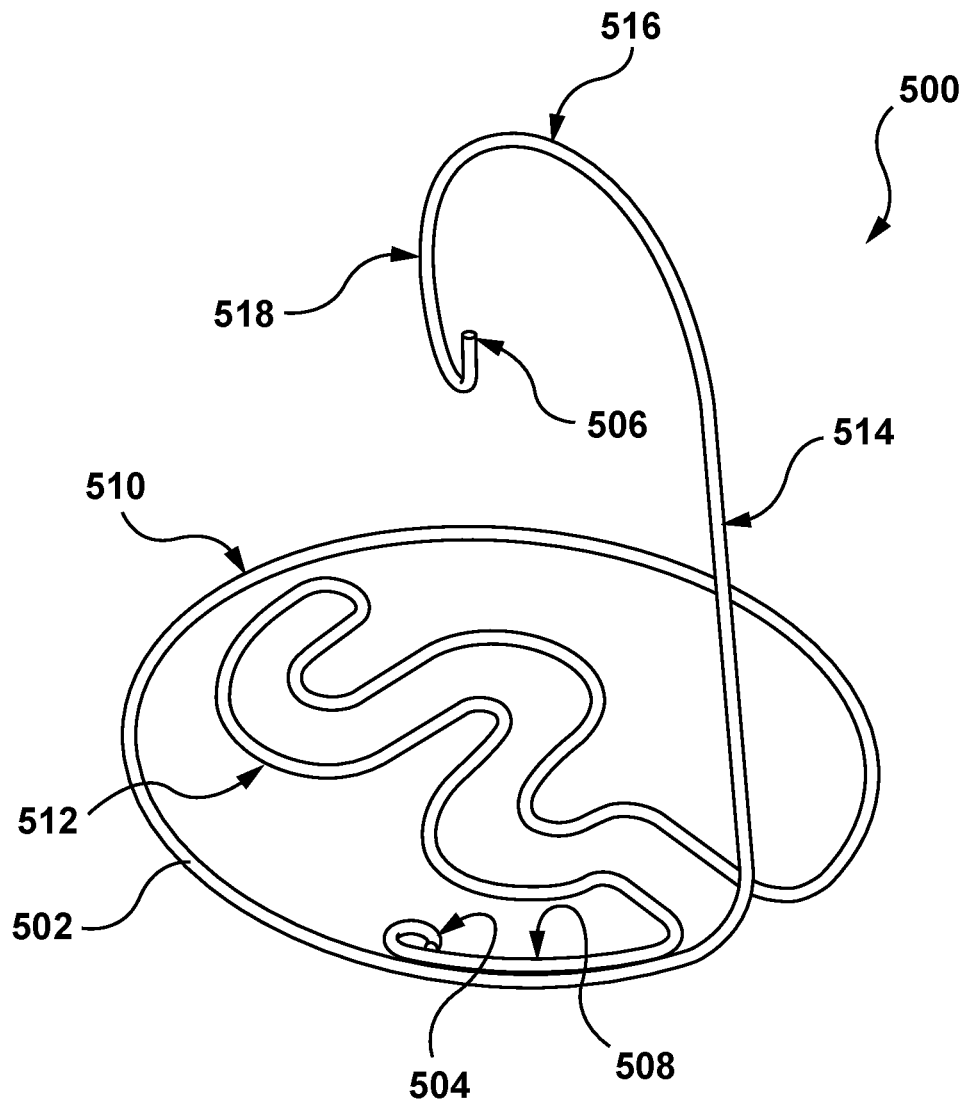
FIG. 5 is a perspective illustration of a prolapse prevention device for treating heart valvular regurgitation in accordance with another embodiment hereof, wherein a leaflet backstop of the prolapse prevention device has a wavy configuration.

As described above, in the embodiment of FIG. 3, the leaflet backstop 312 has a cross or "t" shaped configuration but the leaflet backstop may have other configurations configured to contact at least a first leaflet of a native heart valve in situ. More particularly, FIG. 5 is a perspective illustration of a prolapse prevention device 500 for treating heart valvular regurgitation in accordance with another embodiment hereof, wherein a leaflet backstop 512 of the prolapse prevention device 500 has a wavy configuration. Similar to the prolapse prevention device 300, the prolapse prevention device 500 is formed from a wire-like structure 502 having a first end 504 and a second end 506 that opposes the first end 504. The first end 504 and the second end 506 are disconnected, detached, or otherwise separated from each other. The wire-like structure 502 is a continuous strand or component that is formed from a self-expanding material and is pre-set in its deployed configuration shown in FIG. 5. The wire-like structure 502 is shaped to include an inner tail 508 (which is similar in structure and function to the inner tail 308), a centering ring 510 (which is similar in structure and function to the centering ring 310), the leaflet backstop 512, a vertical support 514 having an apex 516 (which is similar in structure and function to the vertical support 314), and a retrieval arm 518 (which is similar in structure and function to the retrieval arm 318). The leaflet backstop 512 extends radially inward from the centering ring 510 and has a wavy or sinusoidal configuration as shown in FIG. 5. Similar to the leaflet backstop 312, the leaflet backstop 512 preferably extends at a downward or downstream angle from the centering ring 510 to ensure downward pressure on the prolapsing native leaflet.

Figure 6:
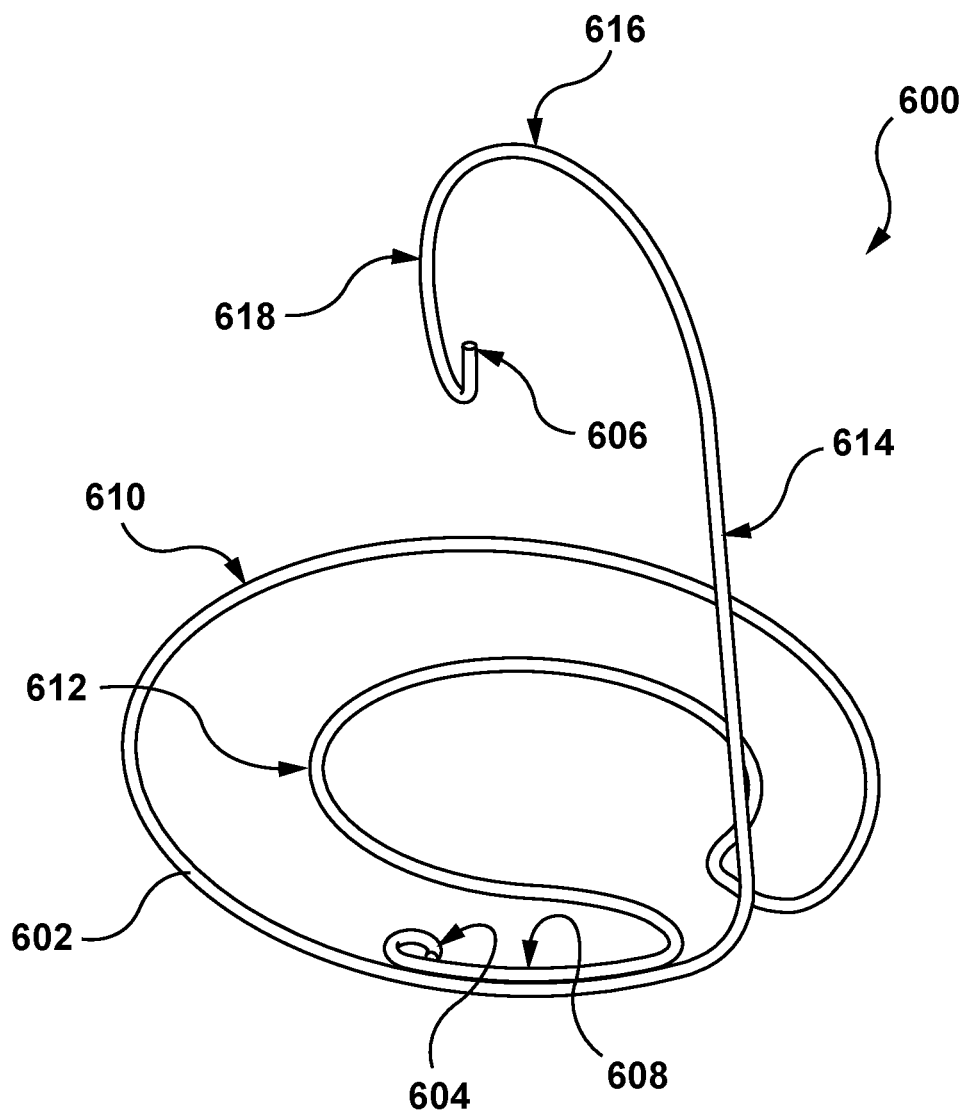
FIG. 6 is a perspective illustration of a prolapse prevention device for treating heart valvular regurgitation in accordance with another embodiment hereof, wherein a leaflet backstop of the prolapse prevention device has a partial ring configuration.

FIG. 6 is a perspective illustration of a prolapse prevention device 600 for treating heart valvular regurgitation in accordance with another embodiment hereof, wherein a leaflet backstop 612 of the prolapse prevention device 600 has a circular or partial ring configuration. Similar to the prolapse prevention device 300, the prolapse prevention device 600 is formed from a wire-like structure 602 having a first end 604 and a second end 606 that opposes the first end 604. The first end 604 and the second end 606 are disconnected, detached, or otherwise separated from each other. The wire-like structure 602 is a continuous strand or component that is formed from a self-expanding material and is pre-set in its deployed configuration shown in FIG. 6. The wire-like structure 602 is shaped to include an inner tail 608 (which is similar in structure and function to the inner tail 308), a centering ring 610 (which is similar in structure and function to the centering ring 310), the leaflet backstop 612, a vertical support 614 having an apex 616 (which is similar in structure and function to the vertical support 314), and a retrieval arm 618 (which is similar in structure and function to the retrieval arm 318). The leaflet backstop 612 extends radially inward from the centering ring 610 and has a partial ring configuration as shown in FIG. 6. Similar to the leaflet backstop 312, the leaflet backstop 612 preferably extends at a downward or downstream angle from the centering ring 610 to ensure downward pressure on the prolapsing native leaflet.

Figure 7:
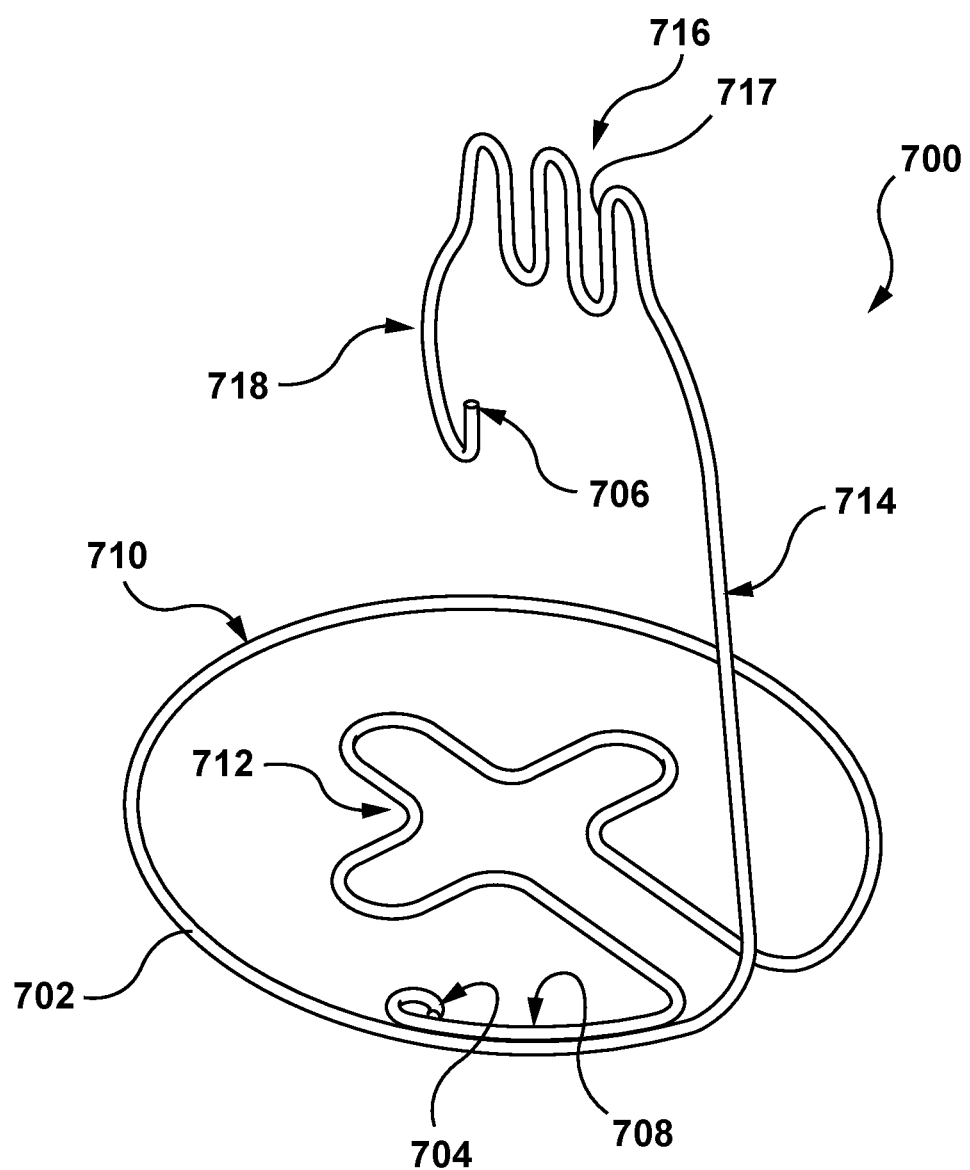
FIG. 7 is a perspective illustration of a prolapse prevention device for treating heart valvular regurgitation in accordance with another embodiment hereof, wherein a vertical support of the prolapse prevention device includes a sinusoidal portion.

In addition, the vertical support may have other configurations beyond the configuration shown in FIG. 3. More particularly, FIG. 7 is a perspective illustration of a prolapse prevention device 700 for treating heart valvular regurgitation in accordance with another embodiment hereof, wherein an apex 716 of a vertical support 714 of the prolapse prevention device 700 includes a sinusoidal portion 717. Similar to the prolapse prevention device 300, the prolapse prevention device 700 is formed from a wire-like structure 702 having a first end 704 and a second end 706 that opposes the first end 704. The first end 704 and the second end 706 are disconnected, detached, or otherwise separated from each other. The wire-like structure 702 is a continuous strand or component that is formed from a self-expanding material and is pre-set in its deployed configuration shown in FIG. 7. The wire-like structure 702 is shaped to include an inner tail 708 (which is similar in structure and function to the inner tail 308), a centering ring 710 (which is similar in structure and function to the centering ring 310), the leaflet backstop 712 (which is similar in structure and function to the leaflet backstop 312), the vertical support 714 having the apex 716, and a retrieval arm 718 (which is similar in structure and function to the retrieval arm 318). The apex 716 of the vertical support 714 has the wavy or sinusoidal portion 717 as shown in FIG. 7. Compared to the apex 316 of the vertical support 314, the apex 716 having the sinusoidal portion 717 has an increased surface area and thus contacts a relatively greater amount of the roof of the atrium for improved bracing of the prolapse prevention device 700. Stated another way, the orientation of the sinusoidal portion 717 is along the roof of the atrium (such that the sinusoidal portion 717 is abutting against and contacting the roof of the atrium) rather than extending up and down within the atrium. Similar to the vertical support 314, the vertical support 714 preferably extends at an upward or upstream angle from the centering ring 710 to minimize obstruction or interference with other anatomic features within the atrium such as the pulmonary veins.

Figure 8:
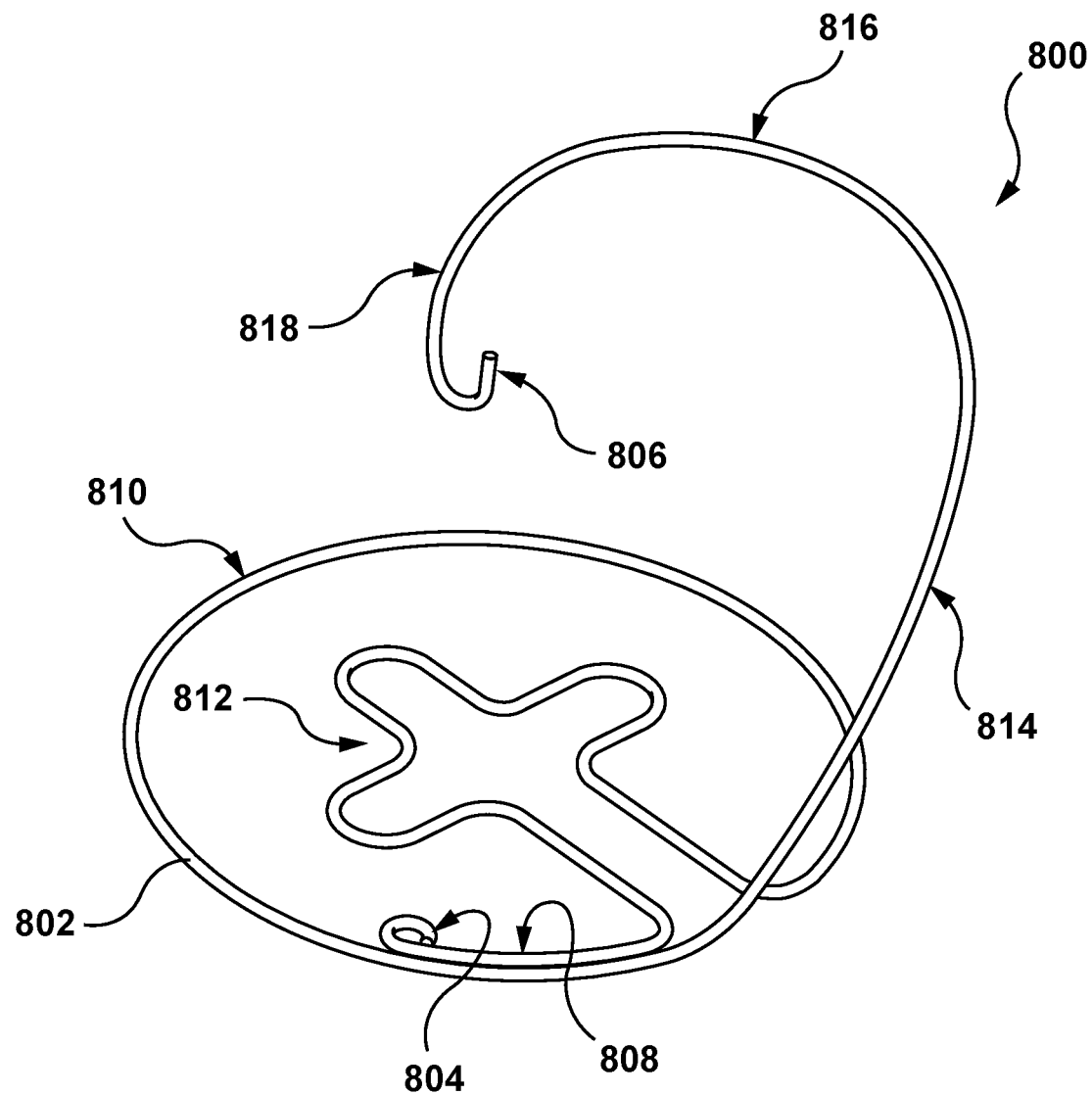
FIG. 8 is a perspective illustration of a prolapse prevention device for treating heart valvular regurgitation in accordance with another embodiment hereof, wherein the vertical support of the prolapse prevention device is curved to be configured to abut against a sidewall of the left atrium of the heart.

In another embodiment hereof, the vertical support may be configured to abut against or conform to at least a portion of a sidewall of the atrium along a length thereof. More particularly, FIG. 8 is a perspective illustration of a prolapse prevention device 800 for treating heart valvular regurgitation in accordance with another embodiment hereof, wherein the vertical support 814 of the prolapse prevention device 800 is curved to be configured to hug or abut against a sidewall of the left atrium of the heart in situ. Similar to the prolapse prevention device 300, the prolapse prevention device 800 is formed from a wire-like structure 802 having a first end 804 and a second end 806 that opposes the first end 804. The first end 804 and the second end 806 are disconnected, detached, or otherwise separated from each other. The wire-like structure 802 is a continuous strand or component that is formed from a self-expanding material and is pre-set in its deployed configuration shown in FIG. 8. The wire-like structure 802 is shaped to include an inner tail 808 (which is similar in structure and function to the inner tail 308), a centering ring 810 (which is similar in structure and function to the centering ring 310), the leaflet backstop 812 (which is similar in structure and function to the leaflet backstop 312), the curved vertical support 814 as described above and having an apex 816, and a retrieval arm 818 (which is similar in structure and function to the retrieval arm 318).

Although embodiments hereof are depicted with a single vertical support, in other embodiments hereof, the prolapse prevention devices described above may include multiple vertical supports, each of which includes an apex configured to seat against a roof of the atrium in situ. Compared to embodiments having a single vertical support, two or more vertical supports may provide improved bracing of the prolapse prevention device.

Figure 9:
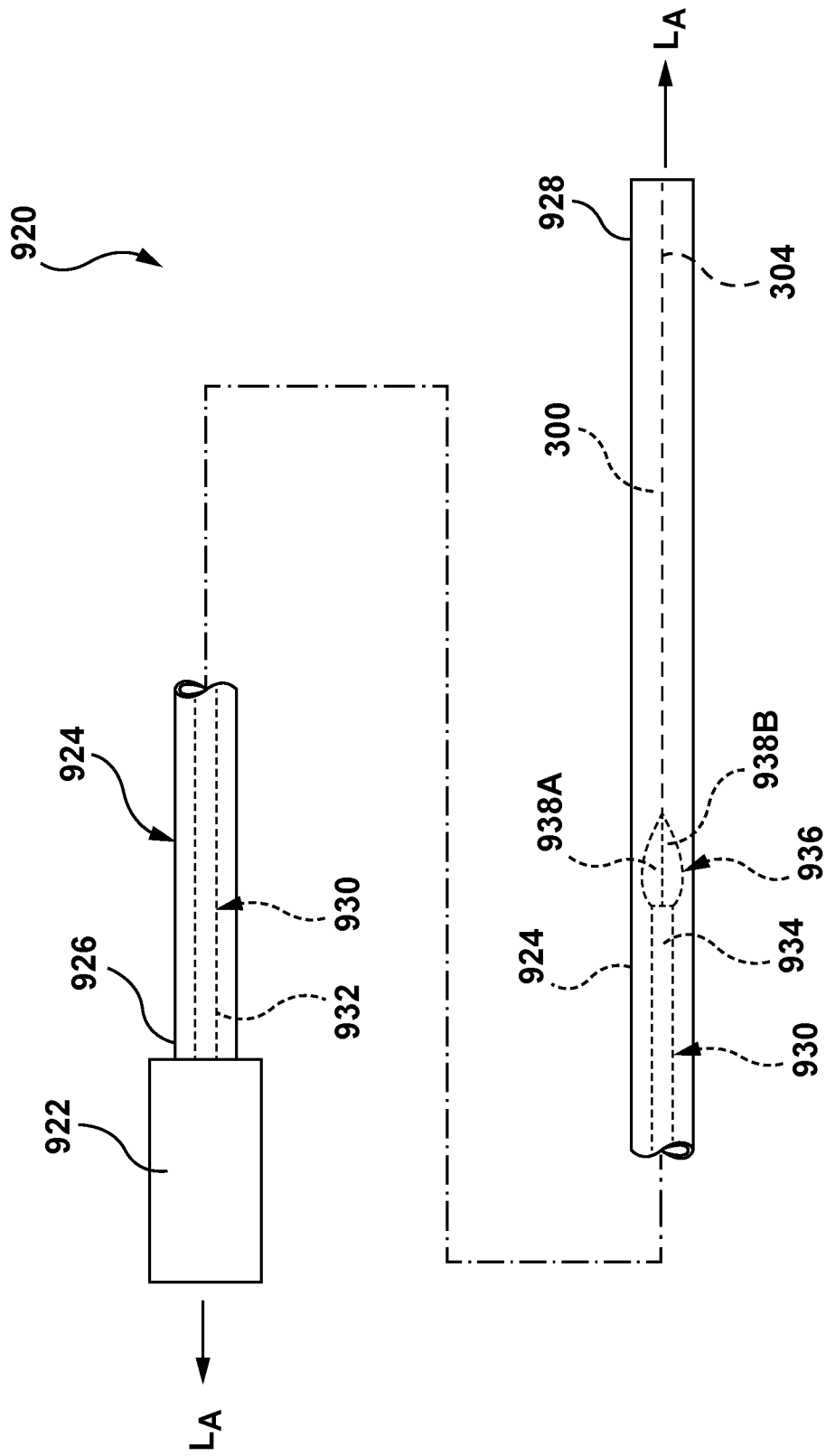
FIG. 9 is a side view illustration of a delivery catheter for delivering the prolapse prevention device according to an embodiment hereof, wherein the prolapse prevention device of FIG. 3 is shown disposed within the delivery catheter in a delivery configuration.

Turning now to FIG. 9, FIG. 9 is a side view illustration of a delivery catheter 920 for delivering a prolapse prevention device according to an embodiment hereof. For exemplary purposes only, FIG. 9 illustrates the prolapse prevention device 300 in a delivery configuration disposed within the delivery catheter 920 but FIG. 9 can similarly be utilized to deliver any embodiment of the prolapse prevention devices described herein. In addition, the delivery catheter 920 is merely exemplary and other suitable delivery devices may be utilized to deliver the prolapse prevention device 300.

Delivery catheter 920 is an elongated device including an outer shaft or sheath 924 configured for delivery through the vasculature, an inner member 930 disposed within the outer sheath 924, and a clasping mechanism 936 disposed at a distal end 934 of the inner member 930 of the delivery catheter 920. More particularly, the outer sheath 924 includes a proximal end 926 which is coupled to a handle 922 at a proximal end of the delivery catheter 920 and a distal end 928 which is positionable at a treatment site in situ. The inner member 930, which is disposed within the outer sheath 924 and moveable relative thereto, includes a proximal end 932 which is also coupled to the handle 922 and the distal end 924. The clasping mechanism 936 is configured to grasp and hold the second end 306 of the wire-like structure 302 of the prolapse prevention device 300, as shown in FIG. 9. The wire-like structure 302 of the prolapse prevention device 300 is held in the delivery configuration via the outer sheath 924, which surrounds and substantially straightens the prolapse prevention device 300 to case advancement thereof through the vasculature to the treatment site within a body vessel. "Substantially straightened" or "substantially straight" as used herein includes wire-like structures that extend parallel to a longitudinal axis LA of the delivery catheter 920 within a tolerance of 15 degrees. Due to the substantially straight or linear delivery configuration of the prolapse prevention device 300, the delivery catheter 920 has a low profile of less than 7 French. In an embodiment hereof, the delivery catheter has a very low profile of 4 French. The very low profile of the prolapse prevention device 300 increases access route options for delivery into the left atrium of a heart, including femoral or radial transseptal access routes as described in more detail herein with respect to FIG. 10. In the substantially straight delivery configuration, the entire length of the prolapse prevention device 300 is disposed within the outer sheath 924. In an embodiment, when in the substantially straight delivery configuration, the length of the prolapse prevention device 300 is between 6-20 inches. In an embodiment, when in the substantially straight delivery configuration, the length of the prolapse prevention device 300 is approximately three times a perimeter of an annulus of a mitral heart valve.

The outer sheath 924 is movable in a longitudinal direction along and relative to the inner member 930 and is user controlled via an actuator (not shown) on the handle 922. When the actuator is operated, the outer sheath 924 is either proximally retracted or distally advanced relative to the inner member 930. Thus, once the prolapse prevention device 300 is properly positioned and it is desired to deploy the prolapse prevention device 300, the outer sheath 924 and the inner member 930 may be moved relative to each other such that the prolapse prevention device 300 is released from the outer sheath 924 and allowed to assume its pre-set or pre-shaped deployed configuration shown in FIG. 3. To cause the relative motion between the outer sheath 924 and the inner member 930, the inner member 930 (as well as the clasping mechanism 936 and the prolapse prevention device 300 held therein) may be distally advanced while the outer sheath 924 is held in place so that the prolapse prevention device 300 is essentially pushed out of the distal end 928 of the outer sheath 924, or the outer sheath 924 may be retracted in a proximal direction while the inner member 930 (as well as the clasping mechanism 936 and the prolapse prevention device 300 held therein) is held in place so that the prolapse prevention device 300 is essentially exposed, or a combination thereof. As the prolapse prevention device 300 exits the outer sheath 924, each integral portion or section of the prolapse prevention device 300 assumes its pre-set or pre-shaped deployed configuration due to the inherent spring restorative force of the wire-like structure 302 of the prolapse prevention device 300.

The clasping mechanism 936 is shown including a pair of jaws 938A, 938B. However, any clasping or snare mechanism suitable to grasp and hold the second end 306 of the wire-like structure 302 may be utilized. In one embodiment, the jaws 938A, 938B are displaceable towards and away from one another and are formed from a resilient material. In an embodiment, the jaws 938A, 938B are biased into a normally open configuration. During delivery to the treatment site or location, the outer sheath 924 extends over the clasping mechanism 936 to maintain the jaws 938A, 938B in a closed configuration as well as to maintain the wire-like structure 302 in a substantially straight delivery configuration as described above. When it is desired to open the jaws 938A, 938B and thereby release the prolapse prevention device 300, the outer sheath 924 is further retracted proximally to expose the jaws 938A, 938B such that their natural bias opens the jaws 938A, 938B and thereby releases the second end 306 of the wire-like structure 302. Other clasping mechanisms may be utilized. For example, and not by way of limitation, the jaws may be opening and closed by a mechanical linkage extending proximally to a handle which is operated by the user. Other clasping mechanisms which do not necessarily include two jaws, may also be utilized such as a snaring hook or snaring lasso.

FIGS. 10-15 are sectional cut-away views of a heart HE illustrating method steps of treating regurgitation at a mitral valve MV via a transseptal approach for delivering and deploying the prolapse prevention device 300 of FIG. 3 in accordance with an embodiment hereof. Access to the mitral valve MV can be accomplished through a patient's vasculature in a percutaneous manner. In an embodiment, the approach to the mitral valve is antegrade and may be accomplished via entry into the left atrium by crossing the interatrial septum. As is known in the art, a guidewire (not shown) may be advanced intravascularly using any number of techniques, e.g., through the inferior vena cava or superior vena cava (FIG. 1), into the right atrium RA through a penetration hole cut in the inter-atrial septum (not shown) and into the left atrium LA (FIG. 1). A guide catheter (not shown) may be advanced along the guidewire and into the right atrium RA, through the penetration hole in the inter-atrial septum, and into the left atrium LA. The guide catheter may have a pre-shaped or steerable distal end to shape or steer the guide catheter such that it will direct the delivery catheter 920 toward the mitral valve MV.

Alternatively, the mitral valve may also be accessed via a transatrial approach for e.g., directly through an incision in the left atrium LA. Access to the heart may be obtained through an intercostal incision in the chest without removing ribs, and a guiding catheter (not shown) may be placed into the left atrium LA through an atrial incision sealed with a purse-string suture. The delivery catheter 920 may then be advanced through the guiding catheter to the mitral valve. Alternatively, the delivery catheter 920 may be modified to include a guidewire lumen such that it may be tracked over a guidewire and placed directly through the atrial incision without the use of a guiding catheter.

Figure 10:
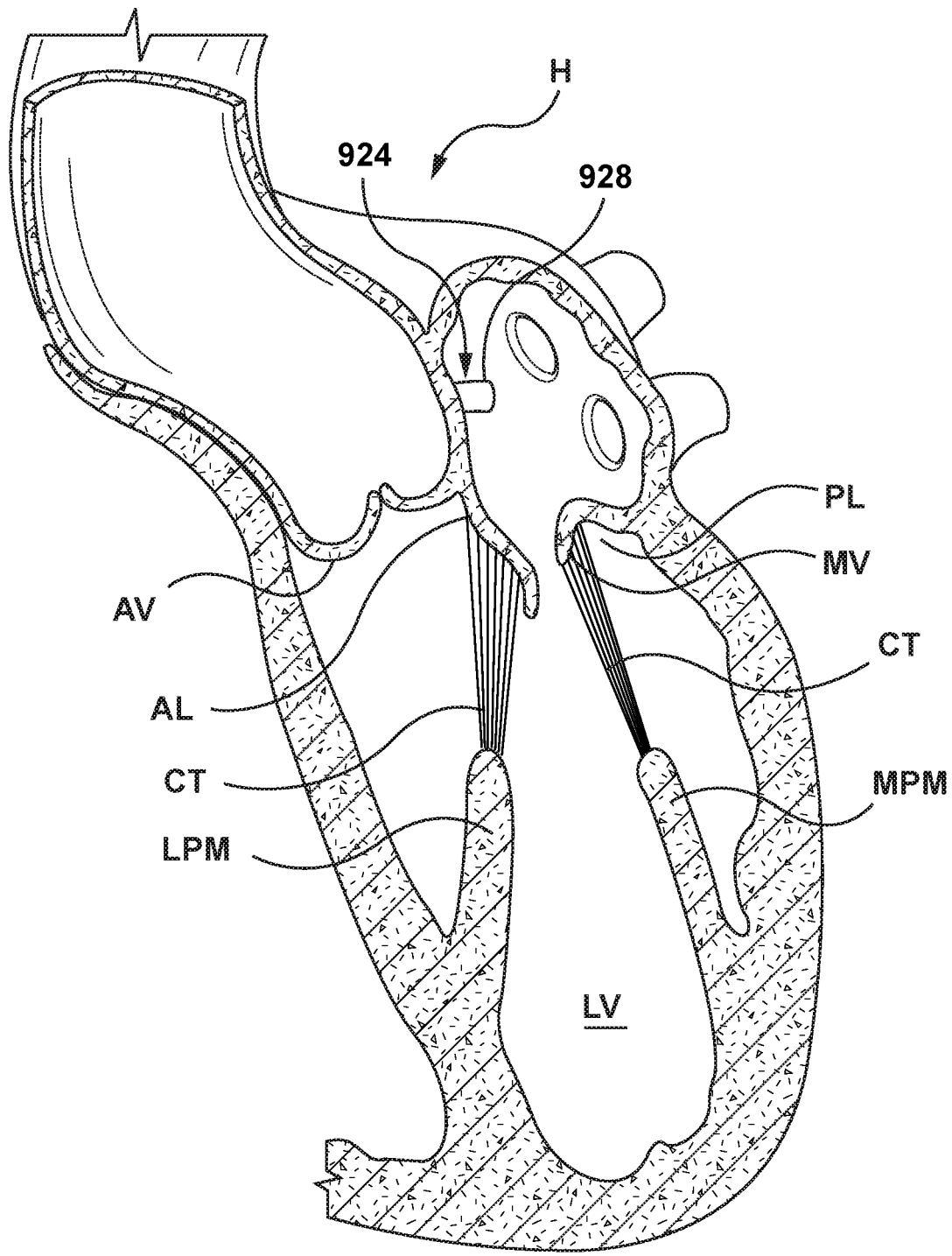
FIG. 10 is a sectional cut-away illustration of a heart illustrating a method step of using the prolapse prevention device of FIG. 3 to repair a prolapsed posterior leaflet of a mitral valve using a transseptal approach in accordance with an embodiment hereof, wherein the delivery catheter of FIG. 9 is positioned within the left atrium of the heart and includes the prolapse prevention device of FIG. 3 in the delivery configuration disposed therein.

Referring to FIG. 10, the distal end 928 of the outer sheath 924 of the delivery catheter 920 is shown positioned in the left atrium LA. The delivery catheter 920 is delivered through the vasculature into the left atrium LA with the prolapse prevention device 300 in the delivery configuration. Intravascular access to the right atrium RA may be achieved via a percutaneous access site in a femoral, brachial, radial, or axillary artery. As will be understood by those knowledgeable in the art, the handle 922 as well as some length of a proximal segment of the delivery catheter 920, are exposed externally of the patient for access by a clinician. By manipulating the handle 922 of the delivery catheter 920 from outside the vasculature, a clinician may advance and remotely manipulate and steer the distal end 928 of the outer sheath 924 of the delivery catheter 920 through the sometimes tortuous intravascular path.

Figure 11:
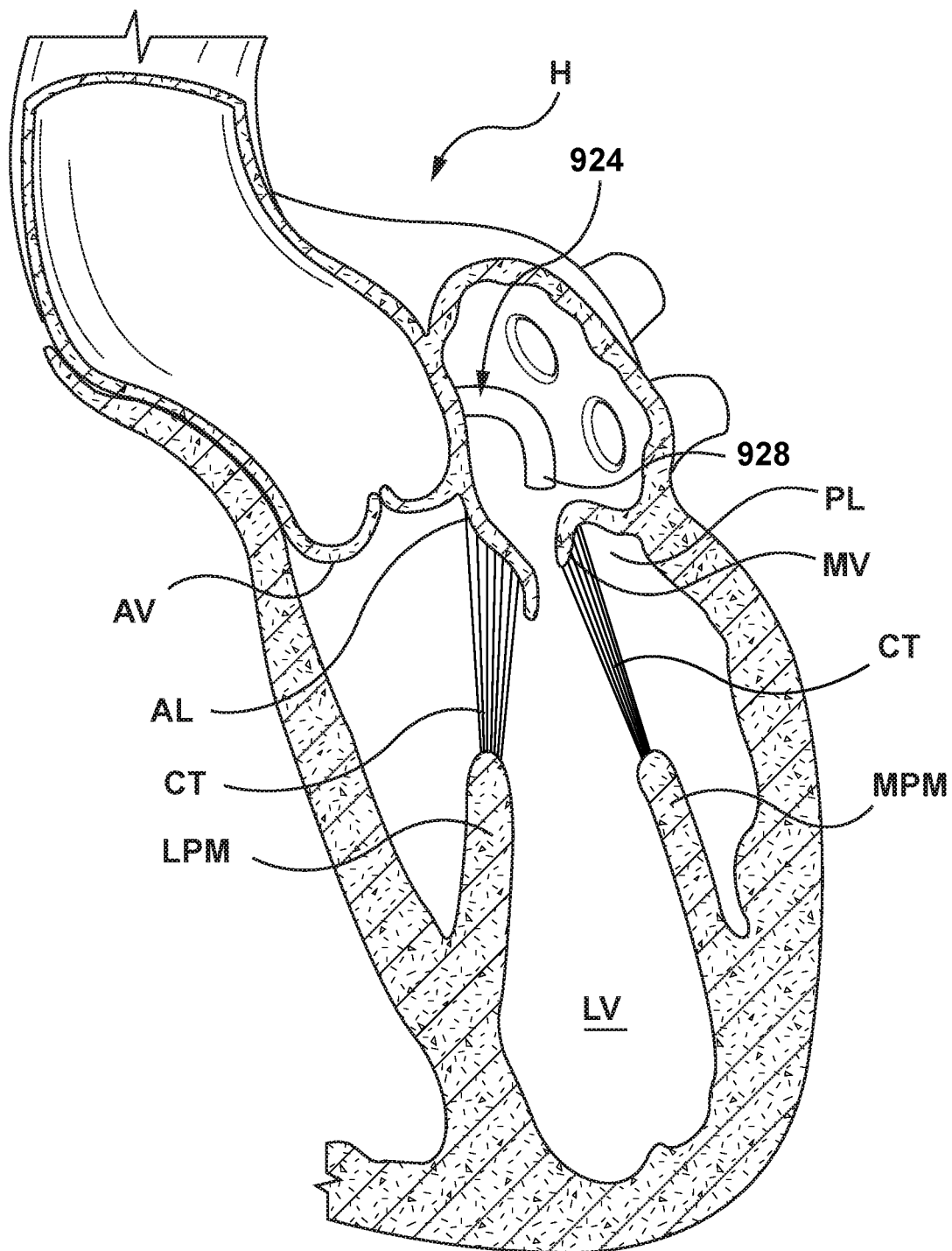
FIG. 11 is a sectional cut-away illustration of the heart illustrating a method step of using the prolapse prevention device of FIG. 3 to repair the prolapsed posterior leaflet of the mitral valve, wherein a distal end of the delivery catheter of FIG. 9 is positioned adjacent to a native mitral valve of the heart.

With reference to FIG. 11, the delivery catheter 920 is distally advanced until the distal end 928 of the outer sheath 924 of the delivery catheter 920 is positioned just above (e.g., adjacent to and upstream of) the mitral valve MV to deliver the prolapse prevention device 300 to the mitral valve MV. Advantageously there is no need to cross the mitral valve MV during deployment of the prolapse prevention device 300, which poses a risk of damaging the native valve leaflets.

Figure 12:
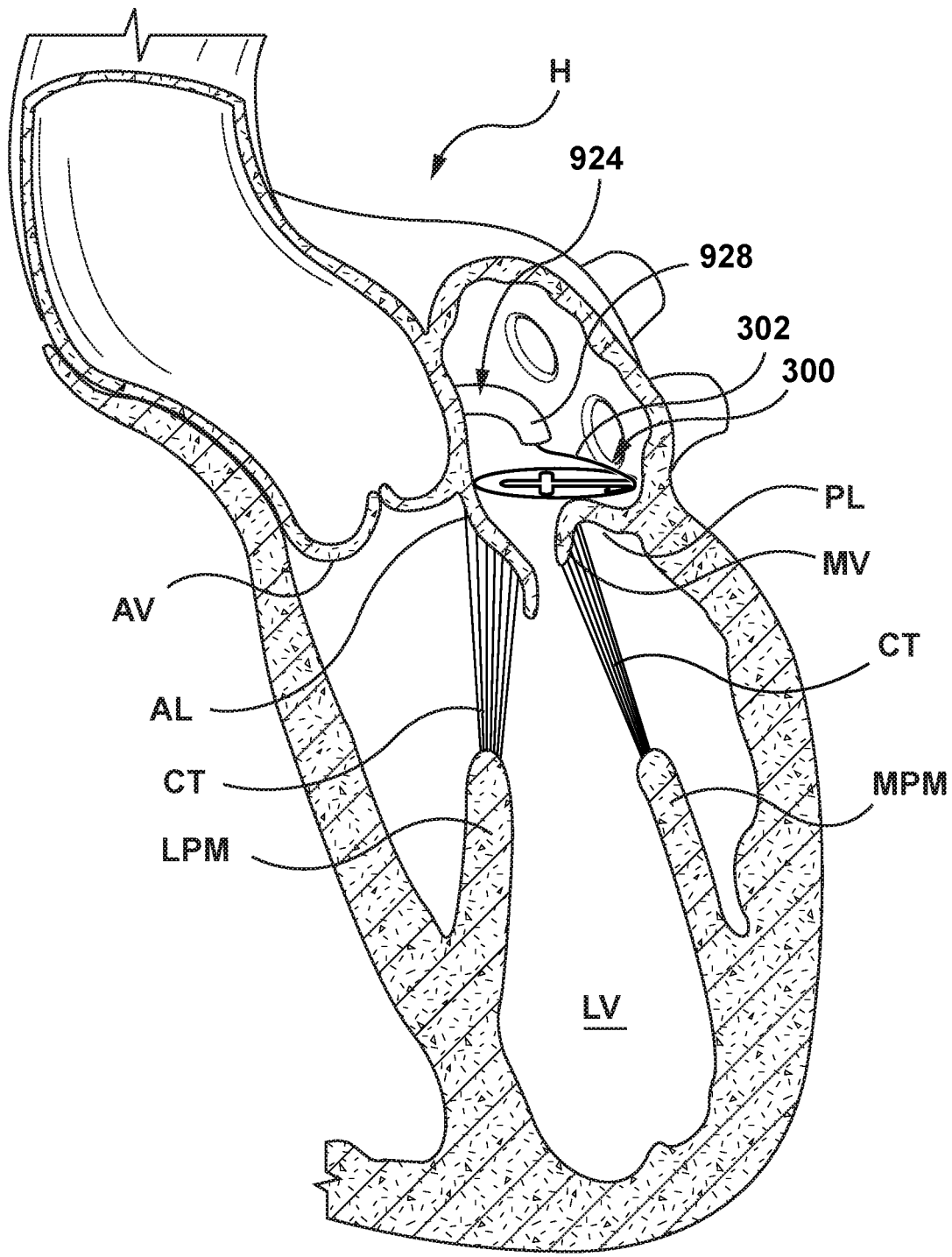
FIG. 12 is a sectional cut-away illustration of the heart illustrating a method step of using the prolapse prevention device of FIG. 3 to repair the prolapsed posterior leaflet of the mitral valve, wherein the delivery catheter of FIG. 9 has been retracted to partially deploy the prolapse prevention device of FIG. 3.

Once the delivery catheter 920 is properly positioned for deployment of the prolapse prevention device 300 as described above, the outer sheath 924 is proximally retracted as shown in FIG. 12 to at least partially deploy the prolapse prevention device 300. Upon retraction of the outer sheath 924, each integral portion or section of the prolapse prevention device 300 assumes its pre-set or pre-shaped deployed configuration due to the inherent spring restorative force of the wire-like structure 302 of the prolapse prevention device 300. In FIG. 12, the first end 304, the inner tail 308, the centering ring 310, and the leaflet backstop 312 are shown deployed while the remaining integral portions of the prolapse prevention device 300 (i.e., the vertical support 314 and the retrieval arm 318) are still disposed within the outer sheath 924.

After partial deployment of the prolapse prevention device 300, a physician may evaluate the positioning of the prolapse prevention device 300 prior to full deployment thereof. "Partial deployment" as used herein includes deployment of at least one integral portion or section of the prolapse prevention device 300. "Partial deployment" as used herein further includes deployment of all integral portions or sections of the prolapse prevention device 300 as long as the second end 306 of the wire-like structure 302 is still held or retained within the clasping mechanism 936 of the delivery catheter 920. Thus, the physician may deploy, for example, approximately 80-95% of the prolapse prevention device 300 and then evaluate the position and suitability of the prolapse prevention device 300 before full deployment thereof. "Full deployment" as used herein includes deployment of all integral portions or sections of the prolapse prevention device 300 as well as the second end 306 of the wire-like structure 302 such that the prolapse prevention device 300 is no longer coupled to a delivery device. If the leaflet backdrop 312 is not exerting sufficient downward pressure to repair the prolapsing native leaflet as desired, the physician can recapture the prolapse prevention device 300 such that the prolapse prevention device 300 can be repositioned and re-deployed.

More particularly, if a physician desires to recapture the prolapse prevention device 300 after partial deployment hereof, the outer sheath 924 is distally advanced to cover and re-constrain the wire-like structure 302. As the outer sheath 924 is advanced over the wire-like structure 302, the wire-like structure 302 resumes its substantially straight delivery configuration. The delivery catheter 920 may be repositioned if desired, and the outer sheath 924 is then proximally retracted to at least partially re-deploy the prolapse prevention device 300 as described above with respect to FIG. 12. The steps of recapturing the prolapse prevention device 300 and at least partially re-deploying the prolapse prevention device 300 may be repeated until the desired positioning of the prolapse prevention device 300 within the left atrium is achieved.

Image guidance, enhanced echogenicity, or other methods may be used to aid the clinician's delivery and positioning of the prolapse prevention device 300. Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's positioning and manipulation of the prolapse prevention device 300 at the target native valve region. For example, such image guidance technologies can be used to aid in determining how much of the prolapse prevention device 300 has been deployed. In some embodiments, image guidance components (e.g., IVUS, OCT) can be coupled to the distal portion of the delivery catheter 920, the guide catheter, or both to provide three-dimensional images of the area proximate to the target heart valve region to facilitate positioning, orienting and/or deployment of the prolapse prevention device 300 within the heart valve region.

Figure 13:
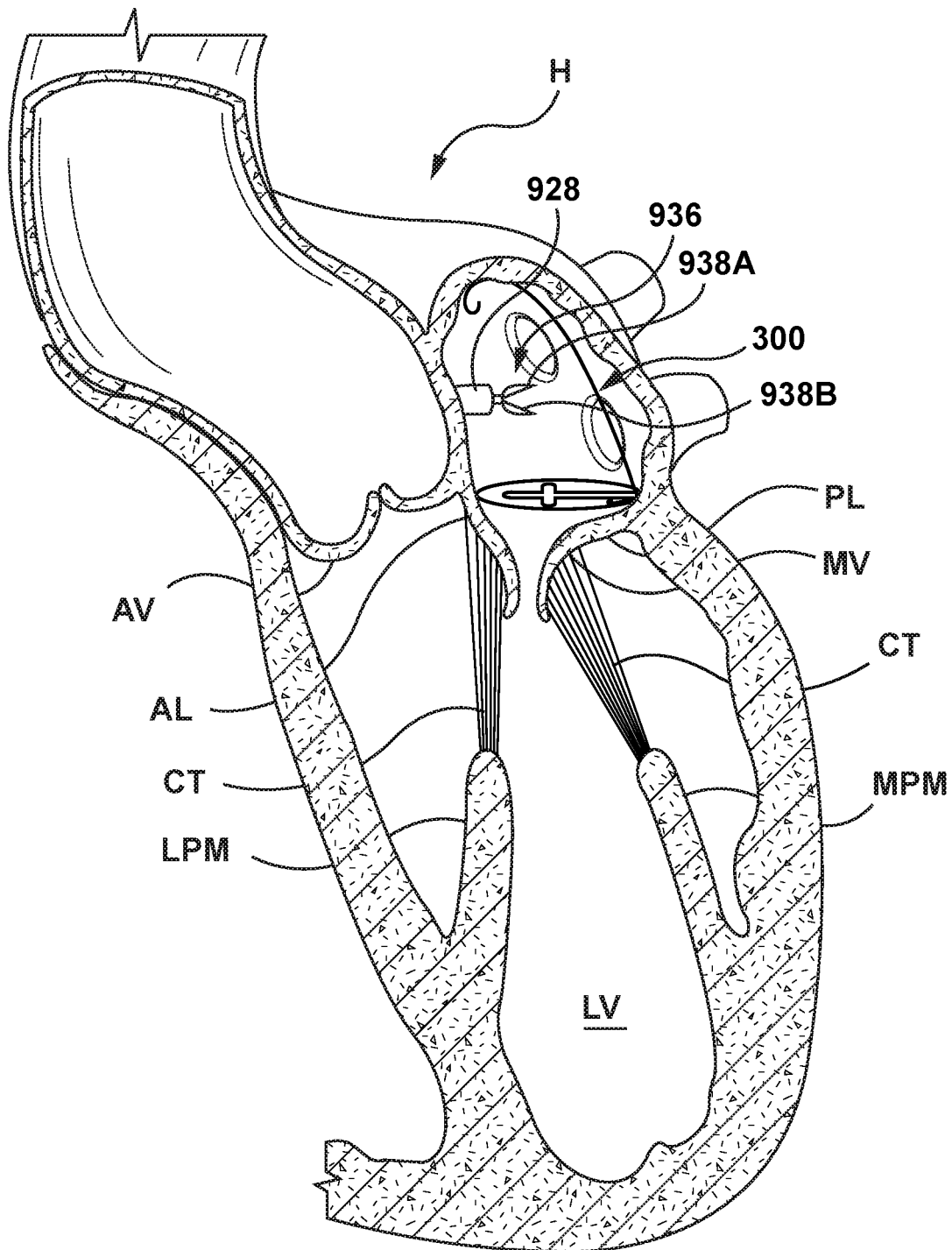
FIG. 13 is a sectional cut-away illustration of the heart illustrating a method step of using the prolapse prevention device of FIG. 3 to repair the prolapsed posterior leaflet of the mitral valve, wherein the delivery catheter of FIG. 9 has been retracted to fully deploy the prolapse prevention device of FIG. 3.

With reference to FIG. 13, after the partial deployment and desired positioning of the prolapse prevention device 300 within the left atrium is achieved, the prolapse prevention device 300 is fully deployed by retracting the outer sheath 924 until the second end 306 of the wire-like structure 302 is released by the clasping mechanism 936 and the prolapse prevention device 300 is no longer coupled to the delivery catheter 920. As shown in FIG. 13, the outer sheath 924 is proximally retracted to permit the jaws 938A, 938B to open and thereby release the second end 306 of the wire-like structure 302. In the deployed configuration, the centering ring 310 of the prolapse prevention device 300 is seated just above, or adjacent to and upstream of, the annulus of the mitral valve MV, the vertical support 314 of the prolapse prevention device 300 extends from the centering ring 310 and the apex 316 thereof is seated against a roof of the left atrium, and the leaflet backstop 312 of the prolapse prevention device 300 extends radially inward from the centering ring 310 and contacts at least the posterior leaflet PL of the mitral valve MV to prevent the posterior leaflet PL from prolapsing into the left atrium. The centering ring 310 and/or the vertical support 314 serve to eliminate or minimize canting of the prolapse prevention device 300, or stated another way, serve to position prolapse prevention device 300 in situ such that after implantation thereof the plane $P_1$ (see FIG. 4) of the centering ring 310 is substantially parallel to a plane of the annulus of the native mitral valve MV.

If desired, the mitral valve MV may be checked for regurgitation after full deployment of the prolapse prevention device 300. Checking for regurgitation of the mitral valve MV may be accomplished by various methods including, but not limited to echocardiogram, to visualize placement of the leaflet backstop 312 and prolapse of the posterior leaflet PL of the mitral valve MV. Accordingly, an echogenic coating may be applied to one or more integral portions of the prolapse prevention device 300 to aid in visualization.

Figure 14:
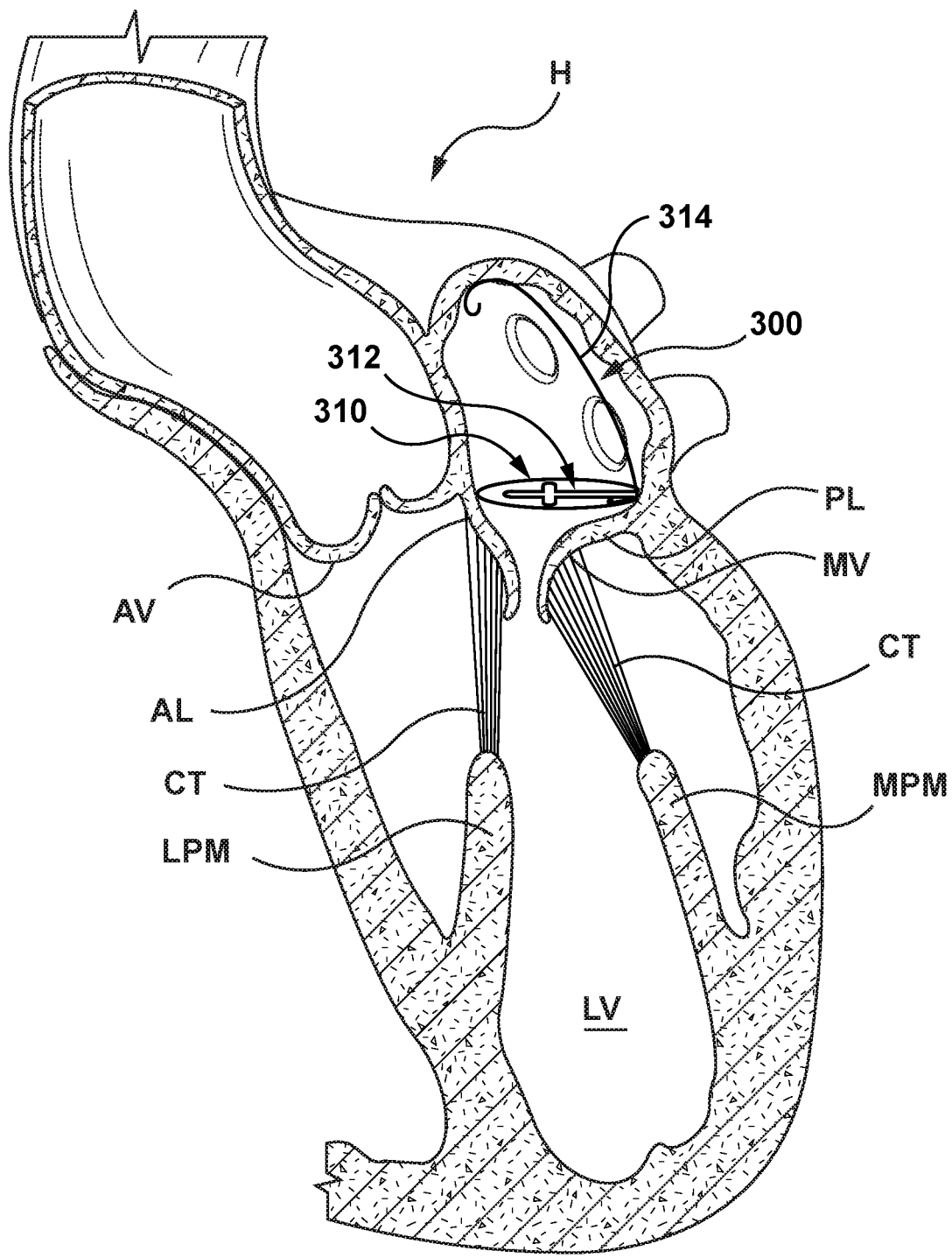
FIG. 14 is a sectional cut-away illustration of the heart illustrating a method step of using the prolapse prevention device of FIG. 3 to repair the prolapsed posterior leaflet of the mitral valve, wherein the delivery catheter of FIG. 9 has been removed from the body and the prolapse prevention device of FIG. 3 remains deployed within the left atrium of the heart in situ.
Figure 15:
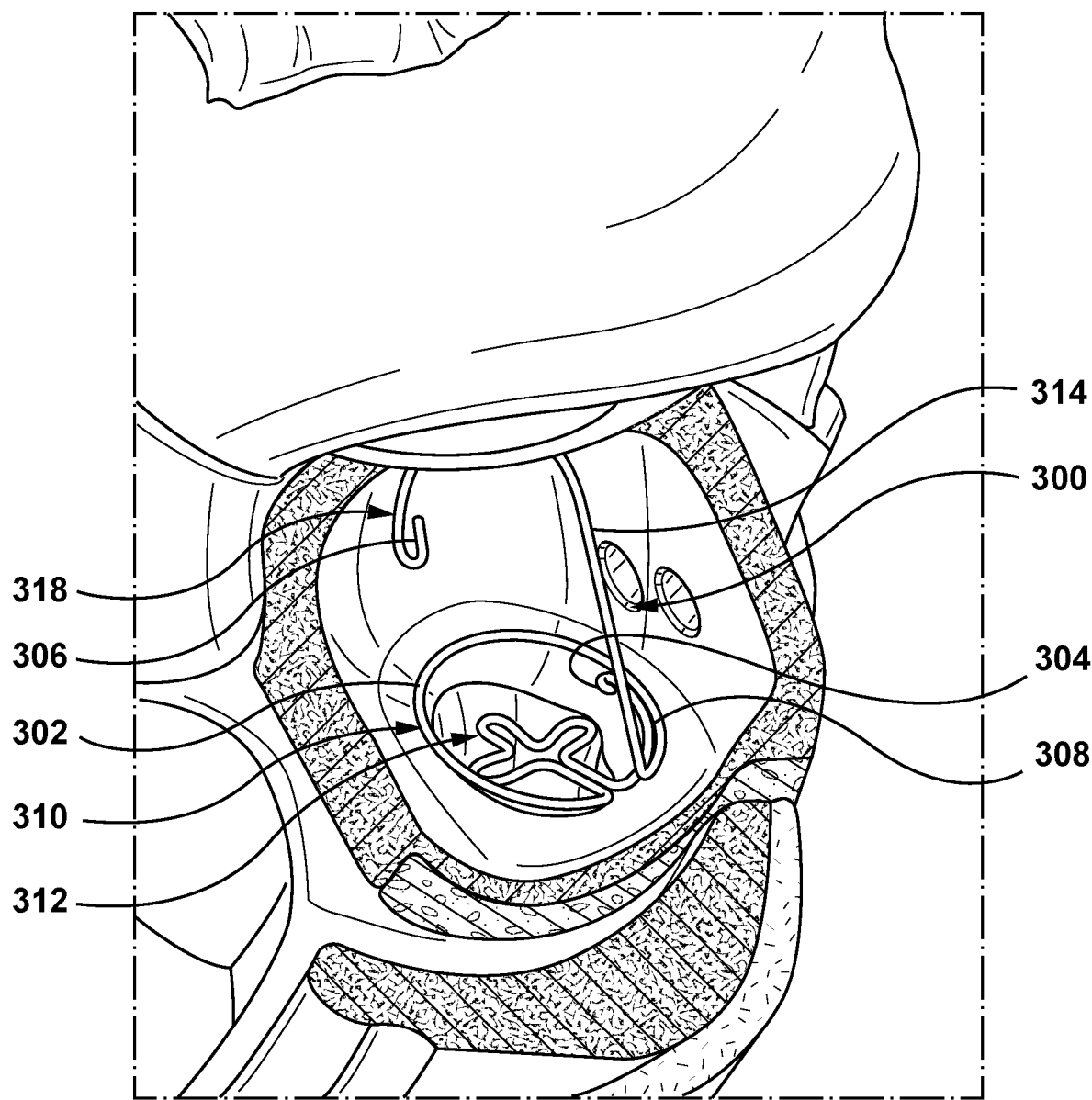
FIG. 15 is an alternative illustration of the prolapse prevention device of FIG. 3 deployed within the left atrium of the heart in situ.

Following full deployment of the prolapse prevention device 300 at the mitral valve MV, the delivery catheter 920 and remaining guidewires (if any) may be removed from the heart H and out of the body of the patient as shown in FIGS. 14 and 15. Notably, the prolapse prevention device 300 remains deployed within the left atrium without any secondary or invasive anchoring components. More particularly, sutures, tines, barbs, or similar anchoring components are not required since the prolapse prevention device 300 as deployed braces itself within the atrium. In addition, the prolapse prevention device 300 as deployed exerts a downward (e.g., downstream) pressure on at least the posterior leaflet and thus there is no need for leaflet capture, which poses a risk of damaging the native valve leaflets. Lastly, the prolapse prevention device 300 as deployed does not reduce or alter the cross-sectional area of the mitral valve MV and thus reduced blood flow through the mitral valve MV is avoided and easy access to the mitral valve MV is still permitted for future therapies and treatments.

While FIGS. 10-15 illustrate the delivery and deployment of the prolapse prevention device 300 at the mitral valve MV, it will be understood that the method steps may be used to deliver and deploy any embodiment of prolapse prevention devices described herein.

The prolapse prevention device 300 is also retrievable after full deployment thereof. More particularly, in the event that the prolapse prevention device 300 needs to be repositioned, removed and/or replaced after implantation, the wire-like structure 302 can transition from the deployed configuration back to the substantially straightened delivery configuration using delivery catheter 920 or a similar snare-type device. The prolapse prevention device 300 is retrievable for a certain time period after full deployment thereof, i.e., is retrievable until the prolapse prevention device 300 has endothelialized. Stated another way, the prolapse prevention device 300 may be removed or repositioned until the prolapse prevention device 300 has endothelialized. For example, it may be desirable to reposition the prolapse prevention device 300 to account for changes in the native anatomy over time.

Notably, the first end 304 and the second end 306 of the wire-like structure 302 are each configured to permit easy retrieval thereof via the delivery catheter 920 or a similar snare-type device because the first end 304 and the second end 306 of the wire-like structure 302 are each formed in the shape of a hook with an integral bend or curve. In addition, in an embodiment, the wire-like structure 302 is radiopaque. In another embodiment, at least the second end 306 of the wire-like structure 302 includes a radiopaque coating. The term "radiopaque" refers to the ability of a substance to absorb X-rays. The radiopaque material or coating allows at least the second end 306 of the wire-like structure 302 to be visible under X-ray or fluoroscopic imaging equipment. Few substances will transmit 100% of X-rays and few substances will absorb 100% of X-rays. For the purposes of this disclosure, radiopaque will refer to those substances or materials which have suitable visibility for retrieval procedures when being imaged by an X-ray imaging device such as but not limited to a fluoroscope.

If a physician desires to retrieve the prolapse prevention device 300 after full deployment and/or implantation thereof, the delivery catheter 920 or a similar snare-type device is delivered into the left atrium. The retrieval process will be described using the delivery catheter 920 although other devices may be utilized. In addition, the retrieval process will be described using the second end 306 of the wire-like structure 302 although the first end 304 may alternatively be utilized. The outer sheath 924 is proximally retracted to expose the jaws 938A, 938B and permit expansion thereof. The opened jaws 928A, 938B are then positioned over the second end 306 of the wire-like structure 302. The outer sheath 924 is then distally advanced to cover and re-constrain the jaws 938A, 938B, thereby closing the jaws 938A, 938B around the second end 306 of the wire-like structure 302. With the second end 306 held within the jaws 938A, 938B, the outer sheath 924 and/or the inner member 930 are moved relative to each other in order to effectively position the wire-like structure 302 within the outer sheath 924 such that the wire-like structure 302 resumes its substantially straightened delivery configuration. After retrieval thereof, the prolapse prevention device 300 may be repositioned and redeployed or may be removed from the patient.

Figure 16:
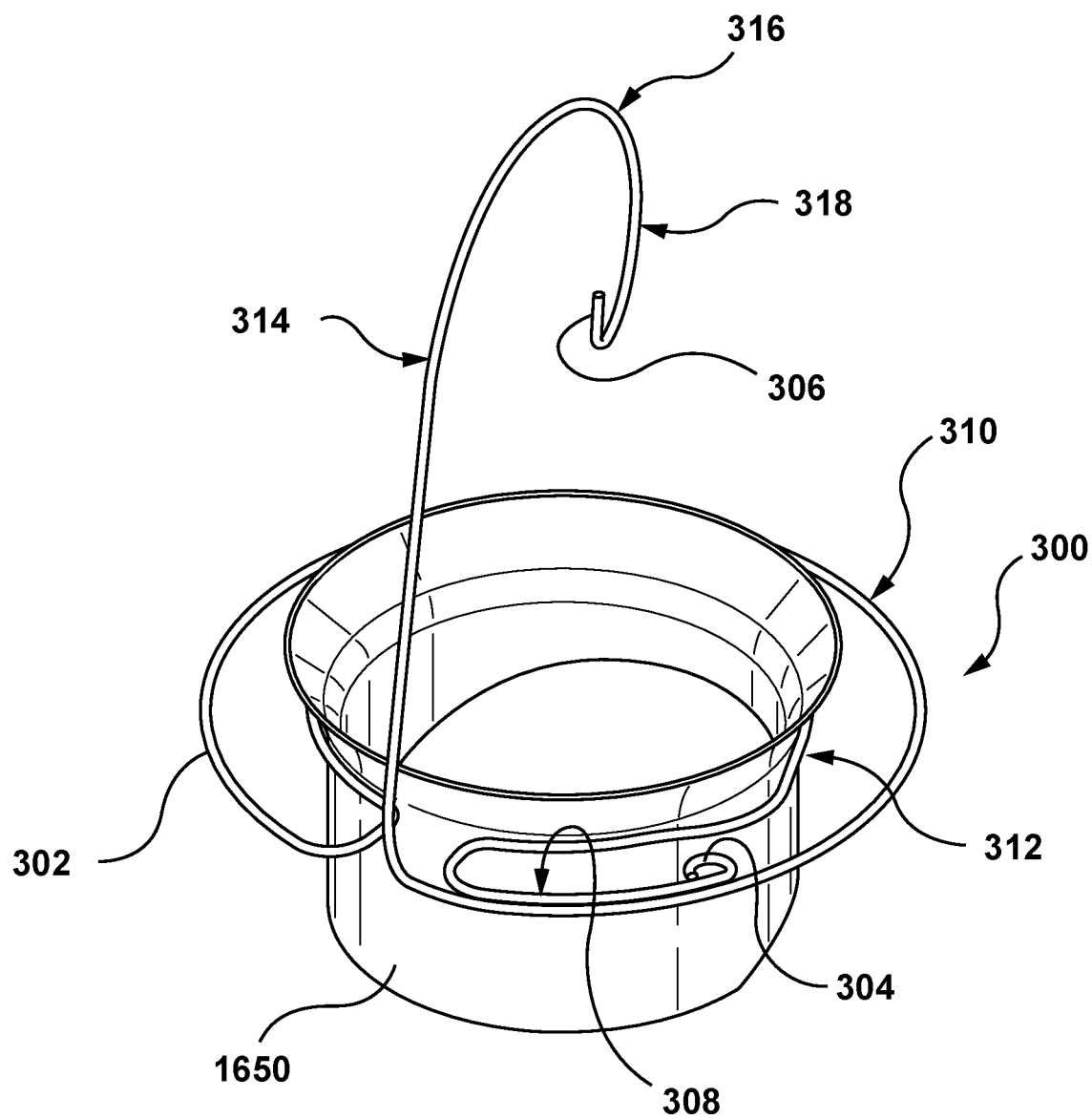
FIG. 16 is a perspective view illustration of a heart valve prosthesis deployed within the prolapse prevention device of FIG. 3 according to an embodiment hereof.

Another advantage of the prolapse prevention device 300 is that it enables subsequent valve replacement after implantation thereof. More particularly, a valve prosthesis may be deployed within the implanted prolapse prevention device 300. The implanted prolapse prevention device 300 serves as a visualization aid for deployment of the valve prosthesis and/or a docking station for the valve prosthesis. For example, as shown in FIG. 16, a valve prosthesis 1650 is shown deployed within the leaflet backstop 312 of the deployed or implanted prolapse prevention device 300. The valve prosthesis 1650 in a compressed configuration (not shown) is percutaneously introduced into a vasculature via a valve delivery device (not shown) and delivered to the implanted prolapse prevention device 300. The valve prosthesis 1650 in the compressed configuration is positioned within the deployed or implanted prolapse prevention device 300, and then the valve prosthesis 1650 is radially expanded or deployed within the leaflet backstop 312 of the deployed or implanted prolapse prevention device 300 as shown in FIG. 16. The leaflet backstop 312 radially expands to accommodate the deployed valve prosthesis 1650, and the deployed valve prosthesis 1650 is held or secured therein.

Figure 17:
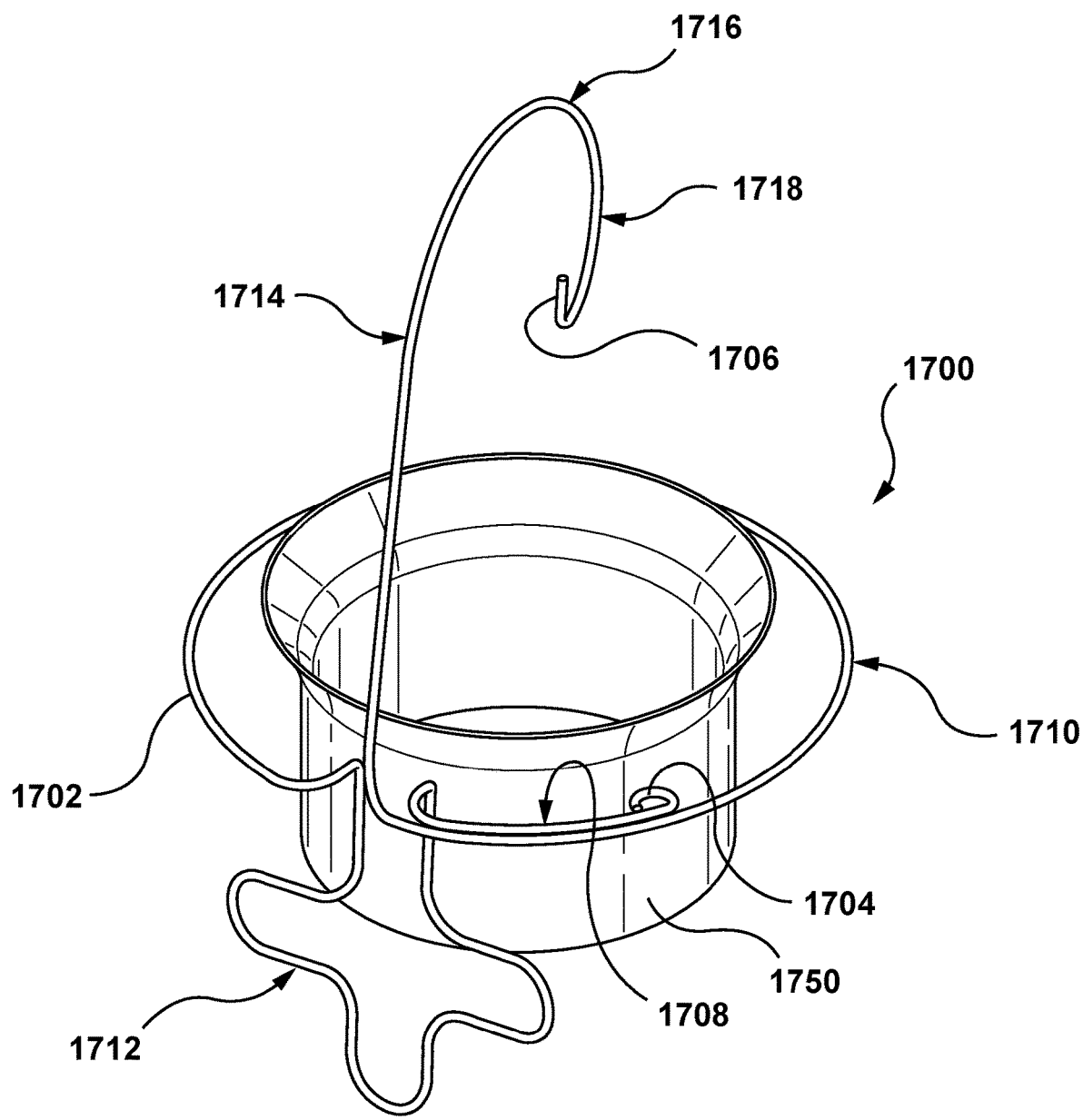
FIG. 17 is a perspective view illustration of a heart valve prosthesis deployed within a prolapse prevention according to another embodiment hereof.

In another embodiment hereof, a valve prosthesis may be deployed within a centering ring of a deployed or implanted prolapse prevention device. For example, as shown in FIG. 17, a valve prosthesis 1750 is shown deployed within a leaflet backstop 1712 of a deployed or implanted prolapse prevention device 1700. Similar to the prolapse prevention device 300, the prolapse prevention device 1700 is formed from a wire-like structure 1702 having a first end 1704 and a second end 1706 that opposes the first end 1704. The first end 1704 and the second end 1706 are disconnected, detached, or otherwise separated from each other. The wire-like structure 1702 is a continuous strand or component that is formed from a self-expanding material and is pre-set in its deployed configuration shown in FIG. 17. The wire-like structure 1702 is shaped to include an inner tail 1708 (which is similar in structure and function to the inner tail 308), a centering ring 1710 (which is similar in structure and function to the centering ring 310), the leaflet backstop 1712 (which is similar in structure and function to the leaflet backstop 312), the vertical support 1714 having the apex 1716 (which is similar in structure and function to the vertical support 314), and a retrieval arm 1718 (which is similar in structure and function to the retrieval arm 318). The leaflet backstop 1712 is similar to the leaflet backstop 312 except that the leaflet backstop 1712 is also configured to bend or pivot in a downward (e.g., downstream) direction when the valve prosthesis 1750 is positioned or advanced through the deployed or implanted prolapse prevention device 1700. The valve prosthesis 1750 is radially expanded or deployed within centering ring 1710 of the deployed or implanted prolapse prevention device 1700 as shown in FIG. 17. The deployed valve prosthesis 1750 is held or secured within the centering ring 1710 of the deployed or implanted prolapse prevention device 1700, and the leaflet backstop 1712 is displaced so as not to interfere with functioning of the valve prosthesis 1750.

Various method steps described above for delivery and deployment of embodiments of the prolapse prevention devices within a native heart valve of a patient may be interchanged to form additional embodiments of the present technology. For example, while the method steps described above are presented in a given order, alternative embodiments may perform steps in a different order. The various embodiments described herein may also be combined to provide further embodiments.

While various embodiments have been described above, it should be understood that they have been presented only as illustrations and examples of the present technology, and not by way of limitation. It will be apparent to persons skilled in the relevant art that various changes in form and detail may be made therein without departing from the spirit and scope of the present technology. Thus, the breadth and scope of the present technology should not be limited by any of the above-described embodiments but should be defined only in accordance with the appended claims and their equivalents. It will also be understood that each feature of each embodiment discussed herein, and of each reference cited herein, may be used in combination with the features of any other embodiment. All patents and publications discussed herein are incorporated by reference herein in their entirety.

What is claimed is:

1. A prolapse prevention device for treating valvular regurgitation in a heart valve, the prolapse prevention device comprising:
   a continuous wire-like structure having a first end and a second end that opposes the first end, the first end and the second end being disconnected from each other,
   wherein the continuous wire-like structure of the prolapse prevention device in a deployed configuration includes
      a centering ring configured to seat adjacent to and upstream of an annulus of the heart valve to circumferentially center the prolapse prevention device in situ,
      a vertical support extending from the centering ring in an upstream direction such that an apex thereof is configured to seat against the atrium and above the annulus of the mitral valve in situ, wherein the vertical support extends longitudinally and non-circumferentially from the centering ring to the roof of the atrium to minimize obstruction within the atrium and wherein the vertical support is curved and configured to abut against a sidewall of the atrium, and
a leaflet backstop extending radially inward from the centering ring and configured to contact at least a first leaflet of the heart valve in situ to exert a pressure in a downstream direction on the first leaflet to prevent the first leaflet from prolapsing into the atrium, and
wherein the continuous wire-like structure from the first end to the second end is substantially straight in a delivery configuration.

2. The prolapse prevention device of claim 1, wherein the heart valve is a mitral heart valve and the first leaflet is a posterior leaflet of the mitral heart valve.

3. The prolapse prevention device of claim 1, wherein the prolapse prevention device is a unitary structure formed from a single piece of material.

4. The prolapse prevention device of claim 1, wherein the continuous wire-like structure is formed from a self-expanding material and is pre-set in the deployed configuration.

5. The prolapse prevention device of claim 1, wherein the centering ring is an open ring and the continuous wire-like structure further includes an inner tail that conforms to an inner surface of the centering ring.

6. The prolapse prevention device of claim 5, wherein the inner tail is configured to permit the open ring to self-adjust to a size of the annulus of the heart valve.

7. The prolapse prevention device of claim 6, wherein the first end and the inner tail lie within the same plane as the centering ring when the prolapse prevention device is in the deployed configuration.

8. The prolapse prevention device of claim 1, wherein the centering ring lies within a first plane and the leaflet backstop lies within a second plane when the prolapse prevention device is in the deployed configuration, the second plane being at an angle between fifteen degrees and seventy-five degrees from the first plane.

9. The prolapse prevention device of claim 1, wherein the leaflet backstop has one of a cross configuration, a circular configuration, and a sinusoidal configuration.

10. The prolapse prevention device of claim 1, wherein the centering ring lies within a first plane and the vertical support lies within a third plane when the prolapse prevention device is in the deployed configuration, the third plane being at an angle between forty-five degrees and eighty degrees from the first plane.

11. The prolapse prevention device of claim 10, wherein the first plane is configured to be substantially parallel to a plane of the annulus of the heart valve.

12. The prolapse prevention device of claim 1, wherein the centering ring lies within a first plane and the vertical support lies within a third plane when the prolapse prevention device is in the deployed configuration, the third plane being at an angle between eighty degrees and one hundred degrees from the first plane.

13. The prolapse prevention device of claim 1, wherein the continuous wire-like structure further includes a retrieval arm extending from the apex of the vertical support in a downstream direction, away from the roof of the atrium.

14. A method of treating heart valvular regurgitation with a system including a delivery catheter and a prolapse prevention device, the method comprising:
percutaneously introducing the system into a vasculature;
delivering the system through the vasculature to a heart valve with the prolapse prevention device in a delivery configuration, wherein the prolapse prevention device is formed by a continuous wire-like structure having a first end and a second end that opposes the first end, the first end and the second end being disconnected from each other, wherein the continuous wire-like structure from the first end to the second end is substantially straight in the delivery configuration;
positioning a distal end of the delivery catheter adjacent to an annulus of the heart valve; and
deploying the prolapse prevention device such that a centering ring of the continuous wire-like structure is seated adjacent to and upstream of the annulus of the heart valve, a vertical support of the continuous wire-like structure extends from the centering ring in an upstream direction such that an apex thereof is seated against a roof of the atrium, the vertical support extending longitudinally and non-circumferentially from the centering ring to the roof of the atrium to minimize obstruction within the atrium, and a leaflet backstop of the continuous wire-like structure is extending radially inward from the centering ring and contacts at least a first leaflet of the heart valve to exert a pressure in a downstream direction on the first leaflet to prevent the first leaflet from prolapsing into the atrium.

15. The method of claim 14, wherein the vertical support is substantially straight and only the apex thereof abuts against a sidewall of the atrium after the step of deploying the prolapse prevention device.

16. The method of claim 14, wherein the vertical support is curved and abuts against a sidewall of the atrium after the step of deploying the prolapse prevention device.

17. A method of treating heart valvular regurgitation with a system including a delivery catheter and a prolapse prevention device, the method comprising:
percutaneously introducing the system into a vasculature;
delivering the system through the vasculature to a heart valve with the prolapse prevention device in a delivery configuration, wherein the prolapse prevention device is formed by a continuous wire-like structure having a first end and a second end that opposes the first end, the first end and the second end being disconnected from each other;
positioning a distal end of the delivery catheter adjacent to an annulus of the heart valve;
deploying the prolapse prevention device such that a centering ring of the continuous wire-like structure is seated adjacent to and upstream of the annulus of the heart valve, a vertical support of the continuous wire-like structure extends from the centering ring in an upstream direction such that an apex thereof is seated against a roof of the atrium, the vertical support extending longitudinally and non-circumferentially from the centering ring to the roof of the atrium to minimize obstruction within the atrium, and a leaflet backstop of the continuous wire-like structure is extending radially inward from the centering ring and contacts at least a first leaflet of the heart valve to exert a pressure in a downstream direction on the first leaflet to prevent the first leaflet from prolapsing into the atrium;
percutaneously introducing a valve delivery device into a vasculature, the valve delivery device including a valve prosthesis disposed at a distal end thereof, wherein the valve prosthesis is in a compressed configuration and the step of percutaneously introducing the valve delivery device into the vasculature is performed after the step of deploying the prolapse prevention device;
delivering the valve delivery device through the vasculature to the heart valve;

positioning the valve prosthesis in the compressed configuration within the deployed prolapse prevention device; and deploying the valve prosthesis within the deployed prolapse prevention device.

18. The method of claim 17, wherein the valve prosthesis is deployed within the leaflet backstop of the prolapse prevention device.

19. The method of claim 17, wherein the valve prosthesis is deployed within the centering ring of the prolapse prevention device.

* * * * *